US012544257B2

(12) United States Patent
NakaMats

(10) Patent No.: US 12,544,257 B2
(45) **Date of Patent: *Feb. 10, 2026**

(54) THERAPY SYSTEM FOR CANCER AND OTHER DISEASES

(71) Applicant: Yoshiro NakaMats, Tokyo (JP)

(72) Inventor: Yoshiro NakaMats, Tokyo (JP)

( * ) Notice: Subject to any disclaimer, the term of this patent is extended or adjusted under 35 U.S.C. 154(b) by 1211 days.

This patent is subject to a terminal disclaimer.

(21) Appl. No.: 17/379,101

(22) Filed: Jul. 19, 2021

(65) Prior Publication Data

US 2021/0338480 A1 Nov. 4, 2021

Related U.S. Application Data

(60) Division of application No. 17/087,813, filed on Nov. 3, 2020, now Pat. No. 11,291,583, which is a (Continued)

(30) Foreign Application Priority Data

May 19, 2016 (JP) ................................ 2016-100547

(51) Int. Cl.

| | |
|---|---|
| ***A61F 7/12*** | (2006.01) |
| ***A61B 18/04*** | (2006.01) |
| ***A61B 90/00*** | (2016.01) |
| ***A61F 7/00*** | (2006.01) |
| ***A61K 41/00*** | (2020.01) |

(Continued)

(52) U.S. Cl.

CPC ................ *A61F 7/12* (2013.01); *A61B 18/04* (2013.01); *A61K 41/0052* (2013.01); *A61N 1/406* (2013.01); *A61N 5/00* (2013.01); *A61N 5/1027* (2013.01); *A61B 2090/3784* (2016.02); *A61F 2007/0002* (2013.01); *A61F 2007/0056* (2013.01); *A61F 2007/009* (2013.01); *A61N 2005/1024* (2013.01)

(58) Field of Classification Search

CPC ................ A61F 7/12; A61F 2007/0056; A61F 2007/009; A61F 2007/0002; A61N 1/406; A61N 5/1027; A61N 2005/1024; A61K 41/0052; A61B 18/04; A61B 2090/3784

See application file for complete search history.

(56) References Cited

U.S. PATENT DOCUMENTS

| | | | |
|---|---|---|---|
| 3,840,019 | A | 10/1974 | Smirnov |
| 5,197,940 | A | 3/1993 | Sievert |

(Continued)

FOREIGN PATENT DOCUMENTS

| | | |
|---|---|---|
| JP | 2003-126275 | 5/2003 |
| JP | 2007-125096 | 5/2007 |

(Continued)

*Primary Examiner* — Joseph A Stoklosa
*Assistant Examiner* — Adam J Avigan
(74) *Attorney, Agent, or Firm* — Wenderoth, Lind & Ponack, L.L.P.

(57) ABSTRACT

[Problem]
The therapy method and the therapy apparatus for difficult cancer such as ductal cancer and other diseases.
[Solution to Problem]
The therapy and the apparatus to beat cancer and other diseases by injecting the material which is energy receptive from outside and emissive heat to cancer cells in the body of a patient, and giving energy from outside.

3 Claims, 41 Drawing Sheets

Related U.S. Application Data continuation of application No. 15/409,539, filed on Jan. 19, 2017, now Pat. No. 11,000,408.

(51) Int. Cl.

| | |
|---|---|
| ***A61N 1/40*** | (2006.01) |
| ***A61N 5/00*** | (2006.01) |
| ***A61N 5/10*** | (2006.01) |

(56) References Cited

U.S. PATENT DOCUMENTS

| | | | | |
|---|---|---|---|---|
| 2007/0130840 | A1 | 6/2007 | Jouhannet | |
| 2007/0250139 | A1* | 10/2007 | Kanzius | A61N 1/406<br>607/100 |
| 2011/0200526 | A1 | 8/2011 | Parsai | |
| 2011/0224479 | A1 | 9/2011 | Yager | |
| 2015/0105687 | A1 | 4/2015 | Abreu | |
| 2016/0015993 | A1 | 1/2016 | Turner | |

FOREIGN PATENT DOCUMENTS

| | | |
|---|---|---|
| JP | 2009-280505 | 12/2009 |
| JP | 2011-032238 | 2/2011 |

* cited by examiner

Fig. 3

Histopathology diagnostic report

The University of Tokyo Hospital Department of pathology / pathology diagnosis

Patient name : Yoshiro NakaMats

Reception date : 2014. 03. 04
Birthday : 1926. 06. 26
85 years and 8 months

Department : Radiology Department Outpatient
Organ : 1.Prostate
Type : Biopsy material Number of organs : 1

Resection date : 2014. 03. 04
: 2014. 03. 08

Pathological diagnosis

Adenocarcinoma of the prostate, needle biopsy (#5,6: referred specimens).
- Ductal adenocarcinoma, Gleason score 4+4=8.

- High-grade prostatic intraepithelial neoplasia (#9).

Findings

Bring specimen, HE stained specimen 3 sheets

「Mishuku Hospital 78997 2011959 Yoshiro NakaMats」
The labels of the three slides are labeled "A 1-4", "B 5-8" and "C 9-12", respectively. Define the one closer to the label of the slide as a younger number, and note the finding below.

2 out of 12, adenocarcinoma is recognized in # 5, 6.
The cylindrical tumor cells exhibit the image of the so-called prostatic duct carcinoma that breeds with a relatively large ductal structure and a fusion gland ductal structure.Some images that adva -nce into existing conduits are also seen. Although the image of normal acinar type adenocarcino -ma breeding with a small ductal structure is slightly observed, most (95% or more) is a duct canc -er component.

Tumor occupation rate and Gleason score are as follows.
#5 Adenocarcinoma, 20%, Gleason score 4+4=8.
#6 Adenocarcinoma, 40%, Gleason score 4+4=8

Also, # 9 acknowledge a small number of atypical ducts equivalent to high-grade Pin (precancerous lesion).

Atypical ducts are not recognized in the other 9.

75
18
71
74

70
17
73
65
47

69
72
51
16

36
29
28
41
51
14
27
21
18
18'
40
66
49
67
12
5
11
15
17
65
46
12
33
47
77
68
76
35
16
51
34
44
5
5
13
13'
48
39
38
13'
25
24
26
37

17 , 65 Device for changing lever pressure 52
53
50
28
29
49
17 , 65
42
51
39
32
43
31
30
43'
68
43
32
31
43'
30
58

Fig. 12

NAME TOBY PROSKY
BIRTHDAY 4/4/76
ADDRESS 1385 YORK AVE NY NY 10021
PHONE (212) 570-9573

- EYE-SIGHT POWER TEST

| | | |
|---|---|---|
| BEFOURHAND | ... | 0.8 |
| NOW | ... | 2.0 |
| INCREASED | ... | 250% |

- MEMORY TEST

| | | |
|---|---|---|
| BEFOREHAND | ............. | 15 |
| NOW | ............. | 30 |
| INCREASED | ............. | 200% |

Fig. 13

NAME ROBERT DELVECCHIO

BIRTHDAY 1-20-41

ADDRESS 236 JAMES ST. FEEDING HILLS, MA.

PHONE 413-786-7967

● CALCULATIN TEST

| | | |
|---|---|---|
| BEFOREHAND | ............. | 84 |
| NOW | ............. | %124 |
| INCREASED | ............. | 148% |

● EYE-SIGHT POWER TEST

| | | LEFT | RIGHT |
|---|---|---|---|
| BEFOURHAND | ... | 1.5 | 0.4 |
| NOW | ... | 2.0 | 1.0 |
| INCREASED | ... | 133% | 250% |

● FULICKER TEST

| | | |
|---|---|---|
| BEFOREHAND | .............. | 13 (point) |
| NOW | .............. | 45 (point) |
| INCREASED | .............. | 346% |

● FATIGUE TEST

| | | YES | NO |
|---|---|---|---|
| BEFOREHAND | .... | 26 | 5 |
| NOW | .... | 8 | 23 |
| INCREASED | ............. | | 400% |

● MEMORY TEST

| | | |
|---|---|---|
| BEFOREHAND | .............. | 22 |
| NOW | .............. | 23 |
| INCREASED | .............. | 105% |

Fig. 14
NAME Omar Goderich
AGE 34 MALE
BEFORE
CALCULATION RESULT
| | |
|---|---|
| Part1 SCORE | 28pt |
| Part2 SCORE | 24pt |
| Part3 SCORE | 31pt |
| Part4 SCORE | 32pt |
| TOTAL SCORE | 115pt |
PLEASE DRAW YOUR FACE
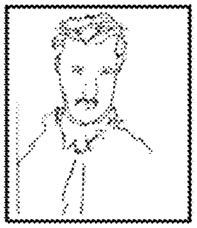
EYESIGHT
| LEFT | RIGHT |
|---|---|
| 1.5 | 1.5 |
AFTER
CALCULATION RESULT
| | |
|---|---|
| Part1 SCORE | 42pt |
| Part2 SCORE | 39pt |
| Part3 SCORE | 39pt |
| Part4 SCORE | 40pt |
| TOTAL SCORE | 160pt |
PLEASE DRAW YOUR FACE
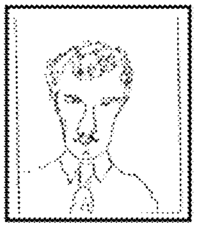
EYESIGHT
| LEFT | RIGHT |
|---|---|
| 2.0 | 2.0 |
RESULT
CALCULATE ···139% IMPROVED

Fig. 15

NAME Mie Mashima

AGE 57 FEMALE

BEFORE

CALCULATION RESULT

| | |
|---|---|
| Part1 SCORE | 43pt |
| Part2 SCORE | 45pt |
| Part3 SCORE | 46pt |
| Part4 SCORE | |
| TOTAL SCORE | 115pt |

PLEASE DRAW YOUR FACE

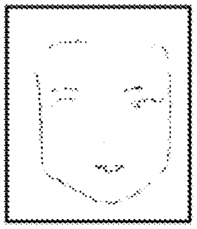

EYESIGHT

| LEFT | RIGHT |
|---|---|
| 0.2 | 0.5 |

AFTER

CALCULATION RESULT

| | |
|---|---|
| Part1 SCORE | 61pt |
| Part2 SCORE | 58pt |
| Part3 SCORE | 60pt |
| Part4 SCORE | |
| TOTAL SCORE | 179pt |

PLEASE DRAW YOUR FACE

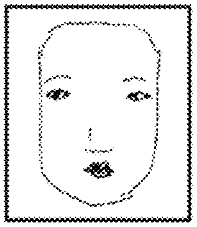

EYESIGHT

| LEFT | RIGHT |
|---|---|
| 0.4 | 0.6 |

RESULT

CALCULATE ···134% IMPROVED

NOTE

Blood pressure is high (100 to 158).
I am tired if I look at fine items,
but I do not use reading glasses.
After the experiment,
the shoulder became lighter,
the visibility became clear.

Fig. 17
NAME
AGE FEMALE
BEFORE
CALCULATION RESULT
| | |
|---|---|
| Part1 SCORE | 36pt |
| Part2 SCORE | 30pt |
| Part3 SCORE | 38pt |
| Part4 SCORE | 40pt |
| TOTAL SCORE | 144pt |
PLEASE DRAW YOUR FACE
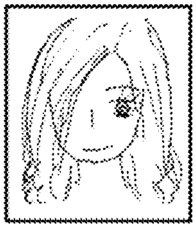
EYESIGHT
| LEFT | RIGHT |
|---|---|
| 0.7 | 0.8 |
AFTER
CALCULATION RESULT
| | |
|---|---|
| Part1 SCORE | 55pt |
| Part2 SCORE | 48pt |
| Part3 SCORE | 50pt |
| Part4 SCORE | 48pt |
| TOTAL SCORE | 201pt |
PLEASE DRAW YOUR FACE
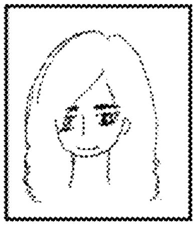
EYESIGHT
| LEFT | RIGHT |
|---|---|
| 0.9 | 0.9 |
RESULT
CALCULATE •••40% IMPROVED
NOTE
I am relaxed and very comfortable.

Fig. 19
NAME ______________
AGE ______________ MALE
BEFORE
CALCULATION RESULT
| | |
|---|---|
| Part1 SCORE | 10pt |
| Part2 SCORE | 12pt |
| Part3 SCORE | 12pt |
| Part4 SCORE | 13pt |
| TOTAL SCORE | 47pt |
PLEASE DRAW YOUR FACE
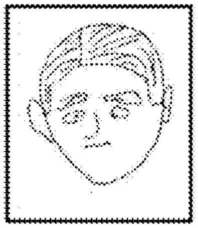
EYESIGHT
| LEFT | RIGHT |
|---|---|
| 0.8 | 1.0 |
AFTER
CALCULATION RESULT
| | |
|---|---|
| Part1 SCORE | 20pt |
| Part2 SCORE | 18pt |
| Part3 SCORE | 18pt |
| Part4 SCORE | 17pt |
| TOTAL SCORE | 73pt |
PLEASE DRAW YOUR FACE
EYESIGHT
| LEFT | RIGHT |
|---|---|
| 1.5 | 1.5 |
RESULT
CALCULATE ···55% IMPROVED
NOTE
Feeling refreshed

Fig. 21

M or F Age : 37 Name : Tadao Ota

| Item | | | |
|---|---|---|---|
| 1 Feel heavy head | ○ | | |
| 2 Feel heavy body | ○ | | |
| 3 Feel heavy legs | ○ | | |
| 4 Yawn | ○ | | |
| 5 Head is blurred | ○ | | |
| 6 Sleepy | ○ | | |
| 7 Eyes get tired | ○ | | |
| 8 Motion is awkward | | | |
| 9 Unstable feet | | | |
| 10 Want to lie down. | | | |
| 11 Thought is not complete | | | |
| 12 Hate to talk | | | |
| 13 Frustrating | | | |
| 14 Distracted | | | |
| 15 Indifference | ○ | | |
| 16 Forgetting | ○ | | |
| 17 Mistakes increase | ○ | | |
| 18 Distracted | ○ | | |
| 19 Sloppy | ○ | | |
| 20 Not persistent | ○ | | |
| 21 Head hurts | | | |
| 22 Getting stiff | ○ | | |
| 23 Low back pain | | | |
| 24 Stuffy | | | |
| 25 Dry mouth | ○ | | |
| 26 Hoarse voice | | | |
| 27 Dizzy | | | |
| 28 Muscle cramps | ○ | | |
| 29 Trembling in limbs | | | |
| 30 Feel sick | ○ | | |
| 31 | | | |
| 32 | | | |
| 33 | | | |
| 34 | | | |
| 35 | | | |
| Number of items marked with ○ | 17 | 0 | |

M or F Age : 57 Name : Tadao Nimachi

| Item | | | |
|---|---|---|---|
| 1 Feel heavy head | ○ | | |
| 2 Feel heavy body | ○ | | |
| 3 Feel heavy legs | ○ | | |
| 4 Yawn | | | |
| 5 Head is blurred | ○ | | |
| 6 Sleepy | ○ | | |
| 7 Eyes get tired | ○ | | |
| 8 Motion is awkward | | | |
| 9 Unstable feet | | | |
| 10 Want to lie down. | | | |
| 11 Thought is not complete | | | |
| 12 Hate to talk | | | |
| 13 Frustrating | ○ | | |
| 14 Distracted | ○ | | |
| 15 Indifference | ○ | | |
| 16 Forgetting | | | |
| 17 Mistakes increase | | | |
| 18 Distracted | | | |
| 19 Sloppy | | | |
| 20 Not persistent | ○ | | |
| 21 Head hurts | | | |
| 22 Getting stiff | ○ | | |
| 23 Low back pain | | | |
| 24 Stuffy | | | |
| 25 Dry mouth | | | |
| 26 Hoarse voice | | | |
| 27 Dizzy | | | |
| 28 Muscle cramps | | | |
| 29 Trembling in limbs | | | |
| 30 Feel sick | | | |
| 31 | | | |
| 32 | | | |
| 33 | | | |
| 34 | | | |
| 35 | | | |
| Number of items marked with ○ | 11 | 0 | |

Test Report

University of Tsukuba
Exercise Physiology Classroom (1) Kräpelinscher Arbeitsversuch Test

Fig. 23

Table 1
Variance analysis table on the results of the Kraepelin test

| Factor | Degree of freedom | Mean square | F |
|---|---|---|---|
| Conditions (Used or Unused) | 1 | 3. 52 | 0. 47 |
| Resting effect (Re and Post of rest) | 1 | 534. 67 | 28. 71 * |
| Individual difference | 11 | 576. 57 | |
| Interaction between condition and rest effect | 1 | 73. 51 | 17. 63 * |
| Interaction between conditions and individual differences | 11 | 7. 54 | |
| Interaction between rest effects and individual differences | 11 | 18. 62 | |
| Interaction between conditions, rest and individual differences | 11 | 4. 17 | |

Fig. 25

Table 2
Variance analysis table on the results of the flicker test

| Factor | Degree of freedom | Mean square | F |
|---|---|---|---|
| Conditions (A) | 1 | 4.38 | 5.03* |
| Resting effect (B) | 1 | 41.26 | 71.14* |
| Individual difference (C) | 11 | 11.39 | |
| A×B | 1 | 13.55 | 104.23* |
| A×C | 11 | 0.87 | |
| B×C | 11 | 0.58 | |
| A×B×C | 11 | 0.13 | |

* Significant at 5% level

Each personal data of frontal region α wave amount

Fig. 27

| NAME \ ITEM | | AGE | TP | ALBUMIN | BILIRUBIN TOTAL | BILIRUBIN DIRECT | BILIRUBIN INDIRECT | GOT | GPT | ALP | CHOLESTEROL | HDL | β-LPO PROTEIN | URIC ACID | UREA NITROGEN | Na | K | Cl | Ca | A/G | WHITE BLOOD CELL | RED BLOOD CELL | HEMOGLOBIN | HEMATOCRIT | $T_3$ | $T_4$ | CORTISOL |
|---|---|---|---|---|---|---|---|---|---|---|---|---|---|---|---|---|---|---|---|---|---|---|---|---|---|---|---|
| SATOSHI TAMAKI | before | 27 | 7.1 | 4.4 | 0.69 | 0.28 | 2.41 | 20 | 7 | 8.0 | 163 | 72.4 | 324 | 114 | 5.6 | 14.5 | 5.0 | 104 | 5.1 | 1.62 | 6700 | 517 | 15.1 | 45.7 | 110 | 9.7 | 6.2 |
| | after | | 7.1 | 4.5 | 0.69 | 0.28 | 0.38 | 14 | 6 | 7.8 | 162 | 72.2 | 327 | 113 | 5.8 | 14.9 | 5.0 | 105 | 5.1 | 1.73 | 6300 | 514 | 15.0 | 45.1 | 116 | 7.7 | 7.0 |
| AKIRA WATANABE | before | 26 | 7.0 | 4.0 | 0.30 | 0.10 | 0.20 | 19 | 23 | 5.0 | 163 | 48.6 | 349 | 119 | 4.9 | 11.4 | 3.6 | 105 | 4.8 | 1.33 | 7500 | 495 | 14.2 | 42.3 | 97 | 8.1 | 5.2 |
| | after | | 7.0 | 4.1 | 0.31 | 0.11 | 0.20 | 19 | 20 | 4.6 | 162 | 46.1 | 324 | 98 | 4.9 | 11.6 | 3.8 | 107 | 4.6 | 1.41 | 7400 | 478 | 13.6 | 40.8 | 99 | 7.7 | 4.8 |
| MANABU OHNUKI | before | 24 | 7.0 | 4.3 | 0.62 | 0.26 | 0.36 | 40 | 13 | 8.4 | 163 | 77.6 | 337 | 96 | 5.0 | 25.1 | 3.9 | 104 | 4.6 | 1.59 | 6500 | 469 | 14.5 | 43.4 | 99 | 6.5 | 5.0 |
| | after | | 6.9 | 4.2 | 0.64 | 0.25 | 0.39 | 33 | 11 | 7.8 | 162 | 73.6 | 330 | 96 | 5.2 | 25.5 | 3.8 | 105 | 4.7 | 1.55 | 6300 | 280 | 14.7 | 44.1 | 104 | 6.3 | 4.2 |
| ATSUSHI TAKAHASHI | before | 25 | 6.8 | 4.4 | 0.57 | 0.22 | 0.35 | 24 | 10 | 5.9 | 163 | 75.8 | 257 | 58 | 4.3 | 19.5 | 4.1 | 104 | 4.9 | 1.83 | 5900 | 474 | 14.5 | 43.1 | 100 | 9.9 | 6.2 |
| | after | | 6.6 | 4.4 | 0.54 | 0.22 | 0.32 | 21 | 15 | 5.7 | 162 | 70.0 | 238 | 42 | 4.4 | 19.3 | 4.2 | 104 | 5.0 | 2.00 | 5300 | 265 | 14.1 | 42.1 | 115 | 9.7 | 5.3 |
| NOBUYUKI OZEKI | before | 24 | 6.7 | 4.1 | 0.43 | 0.17 | 0.26 | 17 | 8 | 9.9 | 163 | 70.9 | 248 | 49 | 4.9 | 21.1 | 4.2 | 106 | 4.6 | 1.57 | 5900 | 512 | 14.4 | 44.5 | 128 | 8.9 | 2.6 |
| | after | | 6.7 | 4.1 | 0.51 | 0.22 | 0.29 | 20 | 10 | 9.5 | 162 | 68.2 | 248 | 48 | 4.8 | 20.9 | 4.4 | 107 | 4.6 | 1.57 | 5800 | 498 | 14.3 | 42.8 | 119 | 10.5 | 4.8 |
| SATOSHI TAKEDA | before | 25 | 7.0 | 4.5 | 0.62 | 0.24 | 0.38 | 19 | 5 | 5.9 | 163 | 78.1 | 502 | 43 | 4.3 | 14.3 | 3.7 | 101 | 5.0 | 1.80 | 7000 | 519 | 16.7 | 48.4 | 127 | 10.3 | 3.4 |
| | after | | 7.2 | 4.5 | 0.63 | 0.22 | 0.41 | 18 | 7 | 5.9 | 162 | 78.2 | 521 | 45 | 4.5 | 13.9 | 3.9 | 102 | 5.2 | 1.66 | 7200 | 524 | 16.9 | 49.7 | 163 | 9.3 | 9.6 |
| YUJI AKIYAMA | before | 23 | 6.9 | 4.0 | 0.77 | 0.38 | 0.39 | 22 | 7 | 12.3 | 163 | 83.1 | 209 | 49 | 4.9 | 20.7 | 3.7 | 107 | 4.6 | 1.37 | 7300 | 450 | 14.0 | 42.8 | 172 | 6.3 | 7.4 |
| | after | | 6.7 | 4.0 | 0.77 | 0.35 | 0.42 | 22 | 9 | 11.8 | 162 | 81.9 | 206 | 48 | 4.8 | 20.5 | 3.6 | 108 | 5.1 | 1.48 | 7000 | 455 | 13.9 | 42.2 | 94 | 6.3 | 5.3 |
| KIMIMITSU SETOH | before | 22 | 6.9 | 4.6 | 0.48 | 0.79 | 0.29 | 21 | 6 | 8.4 | 163 | 70.7 | 222 | 47 | 4.7 | 17.5 | 3.3 | 102 | 4.6 | 2.00 | 5300 | 509 | 14.8 | 44.2 | 94 | 10.1 | 9.5 |
| | after | | 6.8 | 4.3 | 0.43 | 0.17 | 0.26 | 18 | 5 | 7.4 | 162 | 71.6 | 213 | 48 | 4.8 | 17.3 | 3.5 | 103 | 4.5 | 1.72 | 5000 | 482 | 14.3 | 44.2 | 146 | 8.8 | 5.7 |
| OSAMU NIIKURA | before | 24 | 7.4 | 4.6 | 0.48 | 0.19 | 0.29 | 21 | 18 | 5.6 | 163 | 52.0 | 572 | 65 | 6.5 | 13.4 | 3.9 | 105 | 4.7 | 1.64 | 6700 | 536 | 15.0 | 41.8 | 140 | 9.6 | 2.0 |
| | after | | 7.1 | 4.3 | 0.38 | 0.15 | 0.23 | 19 | 15 | 5.4 | 162 | 50.9 | 546 | 67 | 6.7 | 13.2 | 3.9 | 107 | 4.7 | 1.53 | 7200 | 511 | 14.3 | 45.7 | 141 | 10.1 | 6.6 |
| before $\bar{x}$ | | 23.75 | 7.05 | 4.35 | 0.62 | 0.24 | 0.33 | 20.8 | 10.5 | 7.18 | 170.9 | 66.16 | 348.5 | 99.50 | 5.18 | 17.04 | 3.36 | 140.2 | 4.8 | 1.62 | 6642 | 295.2 | 16.72 | 44.13 | 125.5 | 8.8 | 6.28 |
| sd | | 1.83 | 0.21 | 0.32 | 0.22 | 0.29 | 0.15 | 6.35 | 6.02 | 2.26 | 32.54 | 11.65 | 135.5 | 23.67 | 0.71 | 3.79 | 0.42 | 1.14 | 0.17 | 0.19 | 0.771 | 241.3 | 2.25 | 2.25 | 22.52 | 1.2 | 3.54 |
| after $\bar{x}$ | | | 6.91 | 4.28 | 0.58 | 0.23 | 0.35 | 19.6 | 10.1 | 6.83 | 166.7 | 66.00 | 336.8 | 93.75 | 5.24 | 17.07 | 3.9 | 139.9 | 4.7 | 1.63 | 6475 | 285.0 | 14.48 | 43.15 | 132.7 | 8.5 | 5.18 |
| sd | | | 0.18 | 0.15 | 0.18 | 0.07 | 0.12 | 6.50 | 4.64 | 2.14 | 31.8 | 12.21 | 129.8 | 38.57 | 0.71 | 3.76 | 0.42 | 1.38 | 1.30 | 0.15 | 0.780 | 208.1 | 2.45 | 2.45 | 22.80 | 1.3 | 2.33 |

Rev. 1

| | |
|---|---|
| Inspection date : 2016/07/05 | Inspection type : NM |
| Patient ID: 7893101 | Inspection site : Whole body |
| Patient name : Yoshiro NakaMats M 88 years old | Ingress classification: |
| | Request fee : Other |
| Birthday : 1928/06/26 | Request doctor : Yukishige Kyotou |

Self Defense Force Central Hospital 2/2

Fig. 33

NM inspection report

Rev.1

Inspection date 2016/07/05

Inspection type : NM

Patient ID 7893101

Ingress classification

Patient name Yoshiro NakaMats M 88 years old

Request fee : Other

Birthday 1928/06/26

Request doctor Yukishige Kyotou

Clinical diagnosis [Request name]
Prostate cancer, suspected bone metastasis

[Findings]

PET / CT (body trunk) was constructed. Initial examination at our hospital, no comparison image Brachytherapy for prostate cancer has been undertaken.

Long accumulation is seen in prostate cancer, but there is no local accumulation suspected of expensive activity.Although there is a mild absorption increase in CT on the right ischium, FOD accumulation is very light (max SUV: 2.08). There are suspicious changes in cervical vertebrae and thoracolumbar vertebrae, but there are no significant changes in absorption value or significant high concentration in other bones.

Lymph node enlargement of about 2 cm in size is suspected on the right side of the pelvis, but FDG accumulation is mild. (2.93)

Increased accumulation of heart, kidney, renal pelvic ureter, bladder can be explained as physiologic accumulation.

Mild accumulation of gastrointestinal tract can be explained as being within physiological range.

Local lesions that are suspected of metastasis to the cervical chest and abnormal highly accumulated lesions can not be pointed out.

There seems to be accumulation deficiency of FDG in left parietal lobe, which seems to be consistent with the past cerebral infarction.

There is mild accumulation consistent with the soft part shadow of the umbilical level abdominal wall subcutaneous fat weave. Contrast with local findings such as inflammatory accumulation or skin.

[Diagnosis]

Post-treatment brachytherapy for prostate cancer. Right sciatal sclerosis lesion, right pelvic lymph node enlargement.In both cases, FDG accumulation is mild, prostate cancer may be low accumulation, possibility of metastasis is conceivable. Please compare it with the image findings of your hospital and the transition of PSA value.

Described physician Yukishige Kyotou

Date 2016/07/05 Definite physician Yukishige Kyotou

Self Defense Force Central Hospital 1/2

Fig. 34

Patient budget

The Jikei University Hospital

Image diagnosis report

Date of interpretation : 2016/08/09 13:15

Definite physician : Kunihiko Fukuda

[External interpretation request] Report

Print date : 2016/08/15

| | | | |
|---|---|---|---|
| Birthday : | 1928/06/26 | Order number : | 0418708-300621 |
| Sex : | Male | Inspection date : | 2016/08/09 |
| Patient number : | 041-8708-3 | Test species : | External interpretation request |
| Name : | Yoshiro NakaMats | Request department : | 17: Shaping |
| | | Client physician : | Masahito Taneda |
| Shooting items : | Interpretation MRI | Age at inspection : | 88 years old |
| | | Hospitalization or outpatient : | Outpatient |

[Findings] Pelvic MRI

It is the condition after brachytherapy for prostate cancer.
Illegally shaped intramedullary lesions are seen in the posterior pillar of the right acetabulum. The inside of the T1 emphasized elephant is mixed with high signal and low signal with invalid form. In the STIR image, the signal in the high signal area is suppressed. It is probably fat tissue. Because it does not have fat cells in metastatic bone tumor, it is considered as a finding that is consistent with bone infarction. Adjacent cysts are seen, with bone erosion. I think that it is a joint lip cyst, possibly derived from posterior joint lip injury.

At MRI on January 22, 2014 bone marrow is normal. At MRI on November 26, 2014, bone marrow lesions appear in the posterior pillar. The size does not change from the present. Signal strength pattern slightly different from this time. There is a dotted high signal in the in-phase image of the T1 emphasized elephant, and the signal is suppressed in the up-of-phase image. Therefore, it can be seen that it contains a fat ancestral region inside.

[Findings] Intramedullary lesion of posterior acetabular cavern post. Since November 26, 2014, there is no tendency to increase, and since it contains fat tissue inside, it is considered a bone infarction.
A posterior acetabular cup of the posterior acetabular cup. It is accompanied by bone erosion.

[Key image]

Image number 001

Image number 002

Image number 003

Fig. 35

Biological property value

| | Thermal conductivity [W/m°C] | Specific gravity [kg/m³] | Specific heat [J/kg°C] | Calorific value [W/m³] | Blood flow [ml/100mlmin] |
|---|---|---|---|---|---|
| Bone | 2.208 | 1418 | 2092 | 545 | 0.32 |
| Muscle | 0.465 | 1239 | 3724 | 629 | 0.12 |
| Fat | 0.203 | 917 | 2510 | 449 | 0.45 |
| Skin | 1.580 | 1200 | 3390 | 493 | 3.50 |
| Blood | 0.518 | 1056 | 3850 | – | – |

Fig. 41

In vivo heat transfer equation tissue $$\rho c \frac{\partial T}{\partial t} = \lambda \nabla^2 T + \frac{v c_b}{V}(T_a - T) + H_a(T_a - T) + H_v(T_v - T) + M$$

$\rho$: Specific gravity [kg/m³], $c$: Specific heat [J/kg°C], $T$: Temperature [°C], $\lambda$: Thermal conductivity [W/m°C], $v$: Blood flow [kg/s], $V$: Volume [m³], $M$: Calorific value [W/m³], $H$: Coefficient indicating heat transfer [W/m³°C] Subscript $b$: Blood, $a$: Arterial system, $v$: Venous system, $am$: Arterial system of adjacent site, $vn$: Venous system of adjacent site (arterial pool)

$$\rho_b c_b V_a \frac{\partial T_a}{\partial t} = v_a c_b (T_{am} - T_a) + \int_V H_a (T - T_a) dV + H_{av}(T_v - T_a)$$

(venous pool)

$$\rho_b c_b V_v \frac{\partial T_v}{\partial t} = v_v c_b (T_{vn} - T_v) + \int_V \left(\frac{v c_b}{V} + H_v\right)(T - T_v) dV + H_{av}(T_a - T_v)$$

THERAPY SYSTEM FOR CANCER AND OTHER DISEASES

FIELD OF THE INVENTION

The present invention relates to the therapy system for irremediable diseases and more particular Ductal Cancer to make possible to CR (complete response).

BACKGROUND OF THE INVENTION

In Japan, one in two get cancer and one in three die from cancer. Cancer is No. 1 cause of death in Japan. Although new therapy is developed for cancer, and improving a survival rate, however, there is no therapy for Ductal Cancer, because of a few ductal cancer patients.

I, the present invention's inventor suffered very bad Ductal Cancer which has no therapy. And it was declared from a famous doctor that this inventor had only two years left to live. Therefore, the inventor has invented a new therapy at the risk of the inventor's life by doing many experiments and proofs. Accordingly, the inventor applies herewith for a patent according to the results of the inventor's own body in response to the new therapy.

SUMMARY OF THE INVENTION

Technical Problem

Although cancer survival rate improves, there are still incurable cancers. Effective therapy for the ductal cancer has never been established, such as, surgery of total extirpation, which causes incontinence, ED, and cancer metastasis. DA VINCI SURGICAL SYSTEM® needs lowering a head for 8 hours. Thus, there is a risk of losing the eyesight in case of old patients such as in the case of the inventor at 87 years old.

On the other hand, IMRT, VMAT, and Heavy Particle Radiation Therapy have not enough evidence for ductal cancer.

Consequently, these therapies are not expected to help difficult diseases including ductal cancer. In addition, radiation therapy has a risk of puncturing around organs, for example, the intestines and the bladder. Chemotherapy causes side effects such as loss of hair, feeling of tiredness, difficulty in breathing, abnormality of the sympathetic nervous system, sweating, decrease of blood pressure, and an abnormal number of red blood cells.

Other therapies such as High-dose vitamin C therapy is considered effective in America in recent years, however, with regard to its effect on rats but not on humans. In addition, it has a side effect causing skin cancer.

In consideration of the circumstances noted above, the present invention intends to provide new therapy and treatment apparatus for patients suffering incurable cancer such as ductal cancer.

Solution to Problem

Embodiments of the present invention solve the problems noted above by injecting a material to a near place of cancer cells in a body of cancer patients, beforehand.

This material will emit a heat to cancer cells receiving energy from outside, for example, titanium and others. Outside energy, for example, far infrared rays, Laser, radio waves, terahertz (THz) frequencies including LED.

A temperature around the cancer will rise at 41 centigrade to enhance immunity and weaken the cancer. Further raising the temperature of cancer cells at over 42 degrees C., cancer cells will die out because their viable temperature is 42 degrees C. Moreover, the present invention includes the function to remove or ease cancer patient's pains by high temperature.

Advantageous Effects of the Invention

Embodiments of the present invention enhance patient's immunity, and have the effect to be expected CR (complete response) of ductal cancer and other diseases which considered incurable by public known treatments, without side effects, removing pains, also at low cost. Moreover, embodiments of the present invention are effective for patients who are unable to get good result after IMRT, VMAT, Chemotherapy and hormonal therapy. Patients who had the brachytherapy over 5 years and don't have radiate effect also can get therapy of the present invention. In addition, the present invention can be combined with a known therapy. Further, the present invention releases stress and enhances patient's intellectual powers.

This invention's effects has been confirmed by many experiments and practices using many patients for various diseases, for example, spinal stenosis, sciatica, palsy, insomnia, nycturia, dizziness, hypothyroidism, over sensitiveness to cold, backache, diabetes, high blood pressure, palsy after fibroid surgery, dizziness from Meniere disease, angina pectoris, menopausal disorders, osteoporosis, varicose vein, dysautonomia, chronic fatigue syndrome, stop of hypotensive drugs, dropsy swelling, cellulite, body fat burning, itching from dry skin, coxalgia, incontinence, and constipation.

BRIEF DESCRIPTION OF DRAWING

FIG. 3 Medical result of this inventor diagnosed by the University of Tokyo Hospital FIG. 4 Explanation of Ductal cancer FIG. 5 The example of actual equipment to insert materials which receive energy and dispatch heat to cancer FIG. 6 CT picture of the material injected inside of patient body FIG. 7 The materials receivable energy and dispatchable heat at various cutting section of body of this inventor FIG. 8A Energy dispatcher on the abdomen FIG. 8B Energy dispatcher on the buttocks FIG. 8C Energy dispatcher on the waist FIG. 8D Principle drawing of the therapy system of this invention FIG. 9 Side drawing of the therapy apparatus of this invention FIGS. 10A-10B Three dimensional outside picture of the apparatus of this invention FIG. 10C The Concentrator and the body FIG. 10D Power cord FIG. 10E Light behind the knees FIG. 10F Section of 76 of FIG. 10E FIG. 11 The result which improved by the apparatus of this invention FIG. 12 Test result (Russian)

FIG. 13 Test result (Italian)

FIG. 14 Test result (Foreigner scientist)
FIG. 15 Woman test
FIG. 16 Man test
FIG. 17 Woman test
FIG. 18 Man test
FIG. 19 Man test
FIG. 20 Man test
FIG. 21 Test by Inside View Science Academy of Japan
FIG. 22 Experiment by University of Tsukuba (Kraeperin)
FIG. 23 Ditto
FIG. 24 Ditto (Flicker)
FIG. 25 Ditto
FIG. 26 Ditto (Alpha wave)
FIG. 27 Ditto (Blood analysis)
FIG. 28 Ditto
FIG. 29 Ditto (Hormone)
FIG. 30 Ditto
FIG. 31 Actual recorded curve of this inventor used this invention for his body, resulting make PSA 0.01 and healed difficult cancer
FIG. 32 PET-CT image of metastasis to the sciatic and pelvis of the present inventor
FIG. 33 NM Inspection Report—Metastasis to the Sciatic, Pelvis of this invention
FIG. 34 Diagnostic Reports—Eliminate metastasis
FIG. 35 Biophysical property value
FIG. 36 Explanation of therapeutic principle of this invention for metastatic bone tumor
FIG. 37 Human skeleton diagram
FIG. 38 Explanatory diagram of a treatment apparatus of this invention for chest, for example, breast cancer, lung cancer
FIG. 39 Human body side view using the apparatus of FIG. 37
FIG. 40 Explanatory diagram to cool the forehead and face utilizing air conditioner the indoor cooling by using a concentrator
FIG. 41 In vivo heat transfer equation

DESCRIPTION OF EMBODIMENTS

Figure 1:
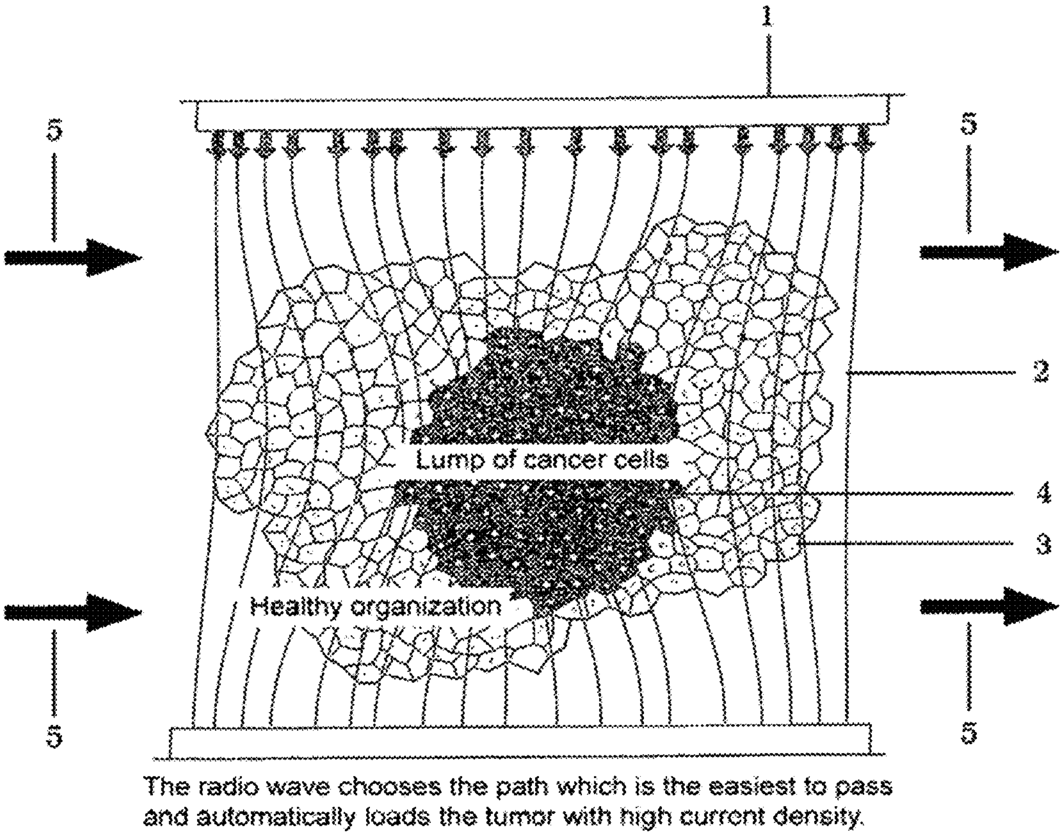
FIG. 1 Explanation drawing of public known Heat therapy

FIG. 1 shows public known cancer treatment known as thermotherapy. This method is maintaining patient's temperature at 39 degrees C. to enhance immunity. This purpose is not killing cancer cells, but stimulating HSP 70 for improving immune system. This thermotherapy is an adjunctive therapy, which cannot kill cancer cells.

Figure 2:
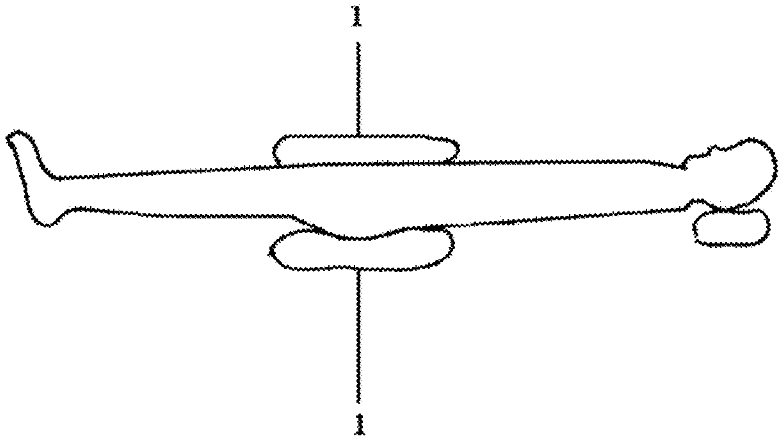
FIG. 2 Explanation drawing of public known Hyperthermia by thermotron

Another cancer treatment public known as Hyperthermia is similar to thermotherapy. This method is expected to destroy cancer cells by RF, laser, and ultrasonic. FIGS. 1 & 2 explain this mechanism. In the FIG. 1, (1) is a Thermotron bolus electrode, (2) is a line current, (3) is a healthy tissue, and (4) is a cancer cell cluster. The best route for radio wave is selected automatically to place high current density stress on tumor (4).

As shown in FIG. 2, this method provides 1500 W energy from two bolus electrodes (1) by radio wave (8~13.56 MHz) system to the diseased portion at a pin point. The aim of this method is generating Joule heat to beat cancer cells, but patient cannot stay by high heat, consequently patient will move from heat source and cannot beat cancer cells effectively. As a result, this therapy is not effective.

Thus, Hyperthermia was treated after using anesthesia. Though this therapy has been studied at University of Kyoto for 20 years, it was not put into practical use. The reason is the fundamental defect based on wrong principle, i.e. this therapy not only gives pain to patient but also because a fact that low temperature blood (e.g. 36 degrees C.) flows around cancer cools cancer (FIG. 1 and FIG. 5), this treatment cannot beat cancer, especially strong bad ductal cancer.

As mentioned above, complete removal of ductal cancer by DA VINCI ROBOT® may cause losing eyesight, incontinence, erectile dysfunction, and metastasis. In the case of ductal cancer, there is no evidence by radiation therapy (only 2 cases and both cases are no proven because patients were dead). Moreover, radiation may damage around organs such as the bowels and the bladder. Chemotherapy has a large side effect and cannot be used for more than 24 months in principle. In addition, for example, a method of injecting a large amount of vitamin C, which is said to be effective in the United States in recent years, for rats, but is not for the human body and has a side effect of causing skin cancer.

The present invention is to beat not usual cancer but very strong and bad cancer such as ductal cancer, which is said to be incurable by chemotherapy of anti-cancer agent, complete removal by DA VINCI ROBOT® and radiation. I, the present invention's inventor got ductal cancer (see FIG. 3 the present inventor's pathology reporting by The University of Tokyo Hospital) and was declared to only have two years I to live (until Dec. 31, 2015) by one of the best 5 doctors in japan.

Therefore, the present inventor has used the present inventor's own body and experimented and completed the present invention at the risk of the present inventor's life, and succeeded to cure ductal cancer.

Figure 4:
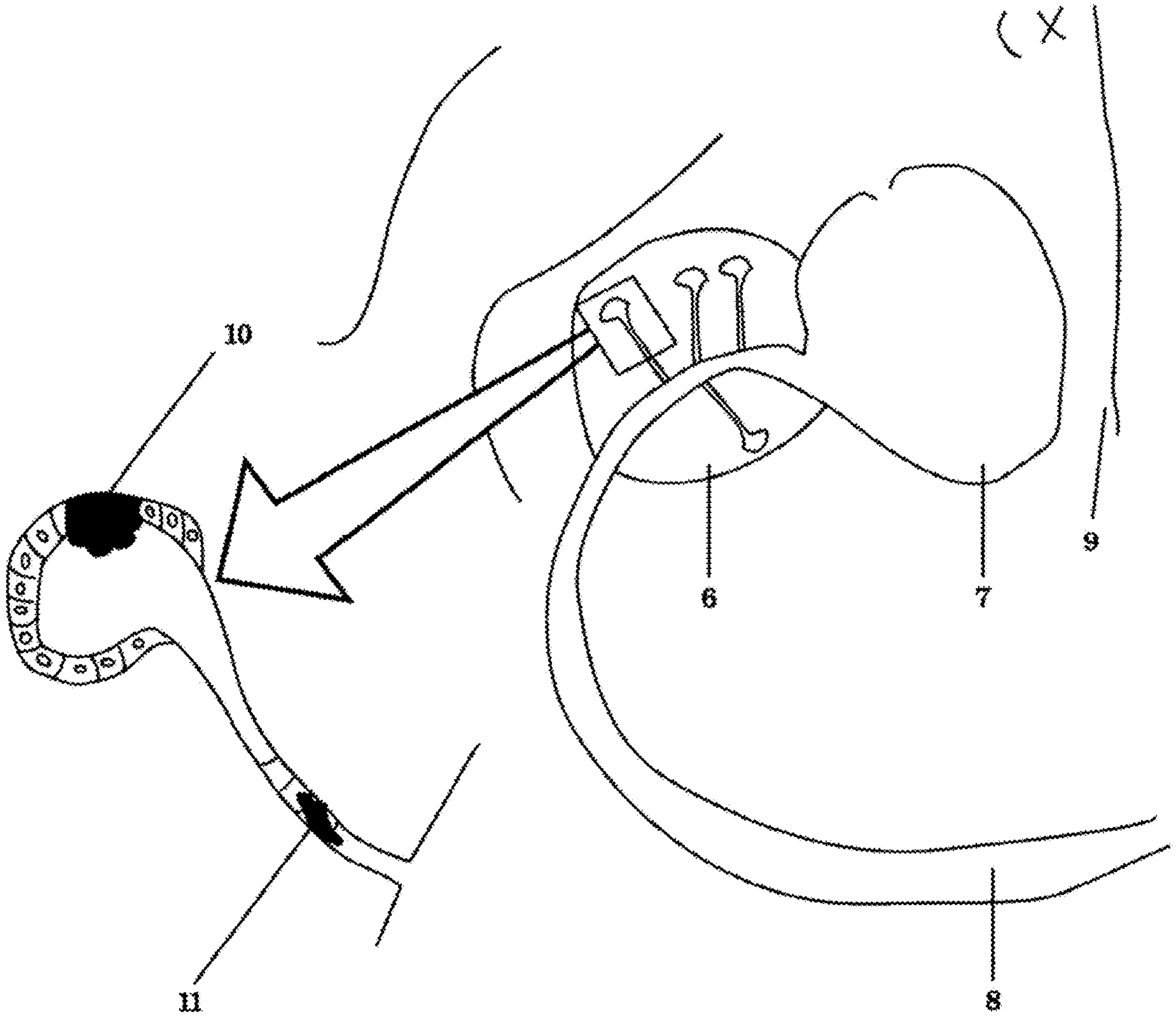

By the way, Ductal Cancer is so uncommon and refractory that some doctors don't know where it is. FIG. 4 shows what Ductal Cancer is. FIG. 4 shows around patient's affected area. In the figure, (6) is prostrate, (7) is bladder, (8) is urethra, (9) is rectum, (10) is the prostate cancer, and (11) is the ductal cancer.

Figure 5:
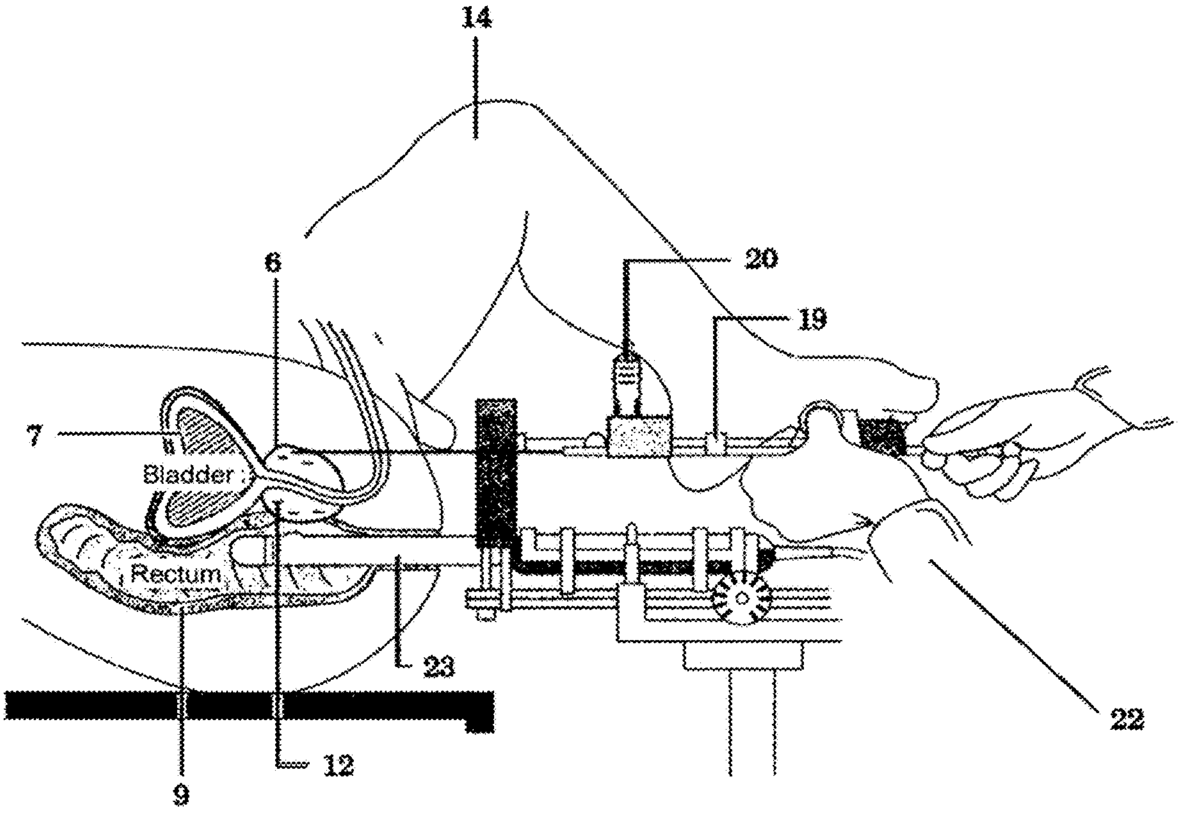

An order of the present invention's therapy method is as follows. First, as shown in FIG. 5, after anesthesia is applied to the lower body of the patient (14), check the inside of the body by a ultrasonic rod (23) and inject a material of this invention into Gun trick (20) by using the applicator (19). It is the same as brachytherapy, but the insert is not an isotope but a biocompatible material, which is energy receptive and beat emissive (12) which is the present invention. A tubular needle is inserted from the perineum into the body around the cancer (11), for example, ductal cancer and the biocompatible material (12) will inject through the needle. (22) is an inserter of the materials of the present invention which receive energy and emit heat to cancer. (12) is the material injected in body as mentioned above. By inserting the ultrasonic probe (23) from anus for observation and shooting camera, deciding position of the material looking computer screen.

Here, the present inventor will explain about an example of the material of this invention of which dimension and number and receive energy from outside and emit to beat cancer. In case of FIGS. 5, 6, and 7 the size is about 4.5 mm in length and 0.8 mm in diameter. The number of this material is, for example, about 50 to 100 pieces. Insert after connecting them in a chain shape, so that they do not scatter by blood flew in the blood vessel. The purpose of the material is to receive energy emitted from outside and store it in the material and remit as heat towards cancer cell and/or blood flow around cancer. Thus, the material should easily receive energy and have high holding power of heat energy.

In other words, this invented material should have the following characteristic, for example, low heat capacity, low heat conductivity, corrosion resistance, light weight, hard heat to shrink, high electrical resistance, no magnetism, MRI is usable at hospital after injection of the material, should not have trouble with physical examination at of customs when traveling abroad, biocompatibility without ion elution in the body and short radioactive half-life if use isotope combination of which describe later.

The present invented material (12) satisfies the above characteristics. For example, Titanium satisfies these conditions. This invented material is not limited to Titanium, but other material including liquids and chemically and all of the following are included in the present invention. Using Titanium only or using Isotope Iodine 125 putted Titanium (Brachytherapy) that emits radiation to the cancer cell—are also included in the present invention.

Treatment with Brachytherapy, and then combining this invented therapy, or combination with the therapeutic method of this invention, or using a brachytherapy material that has already passed half-life period (The radiation self-life is 6 month, and disappear after one year), or using a Titanium before giving the radioactivity are also included in present invention therapy. Additional use of other treatment, for example, IMRT, VMAT, heavy particle radiation, hormonal therapy, anticancer drugs, and molecular targeting medicine are also included in the present invention.

Figure 6:
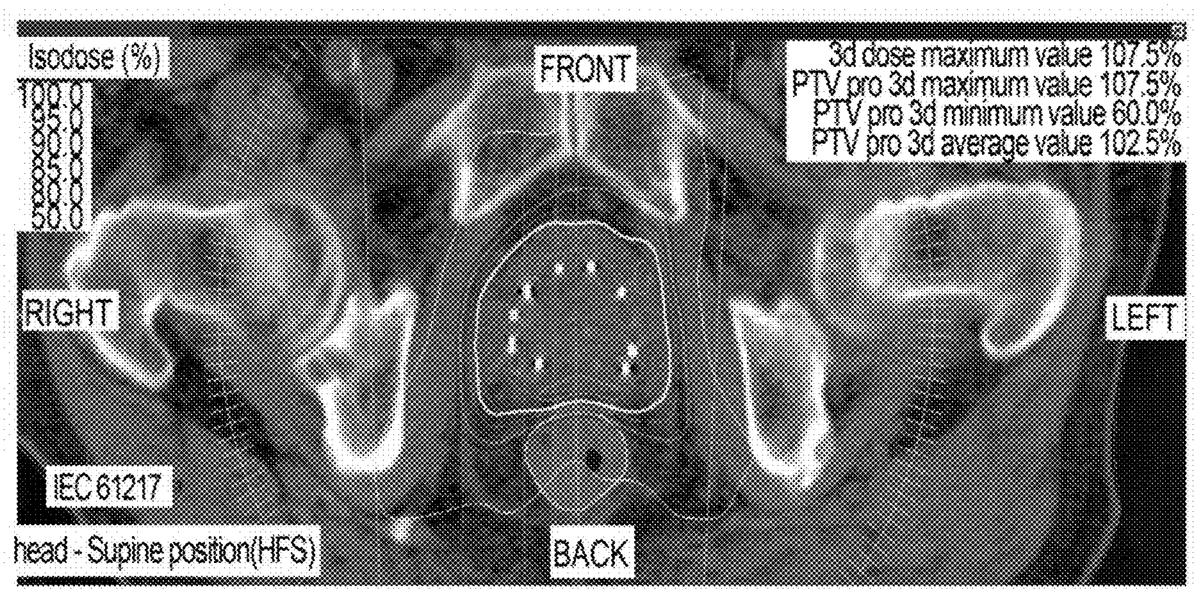
Figure 7:
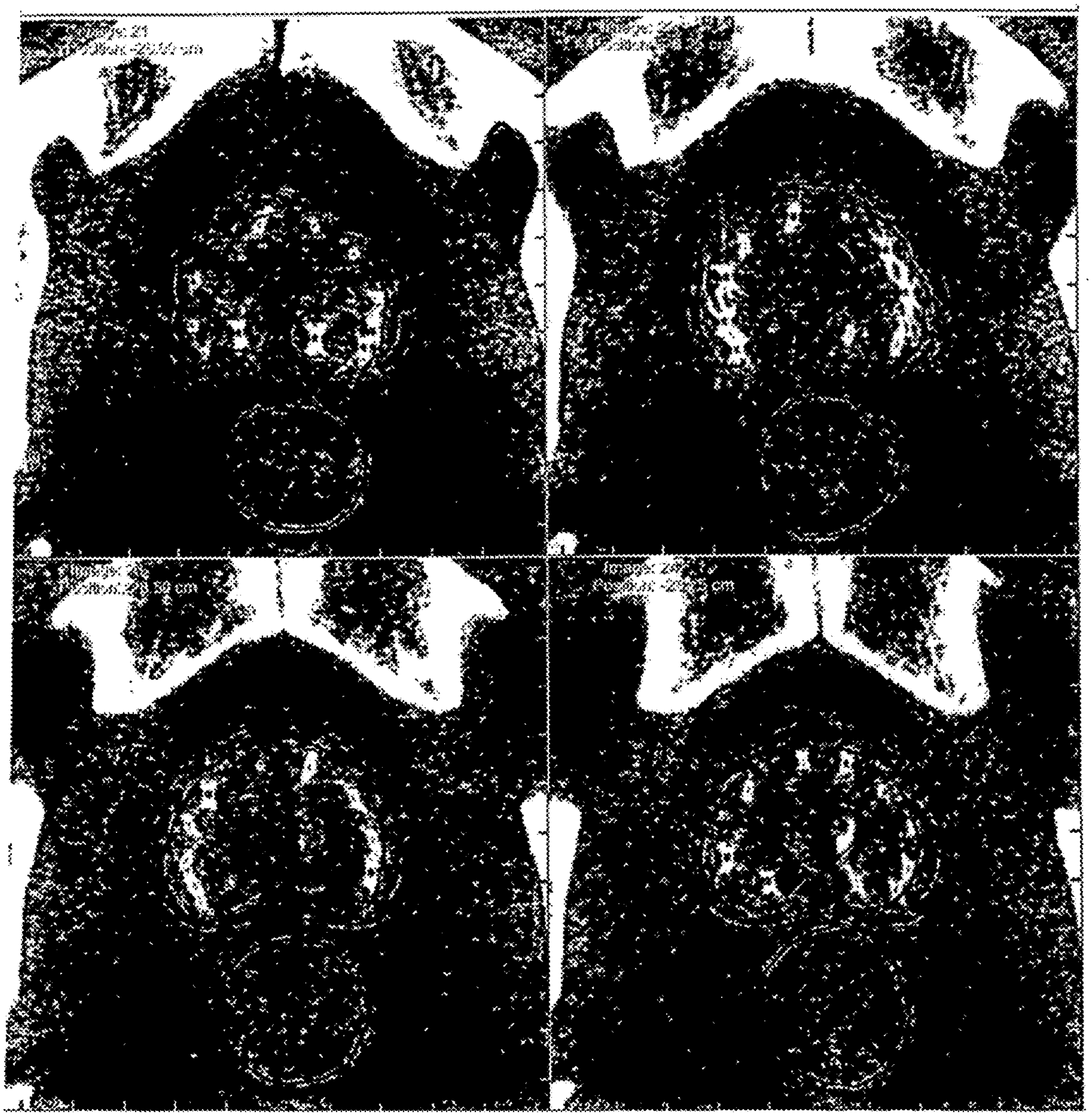

FIG. 6 is the MRI image after injection of the present invented biocompatible material, which is described in FIG. 5. FIG. 7 shows an injected state of the inside of the body viewed from a plurality of cross sections, and present invented biocompatible materials 12 are shown with white dots and these are inserted surrounding the ductal cancer. The present invention is the therapy which increase immunity by heating up to 41° C. and beats cancer cells at 42° C. utilizing the property of protein solidifies at 42° C. which is public known.

As described above, the present invention is completely different from public known heat treatment such as Hyperthermia. Moreover, this invention can be used together with Brachytherapy, alpha-ray injection, hormonal therapy, chemotherapy, IMRT, and VMAT. These cases are also included in the present invention as described above.

Figures 8A, 8B, 8C, 8D:
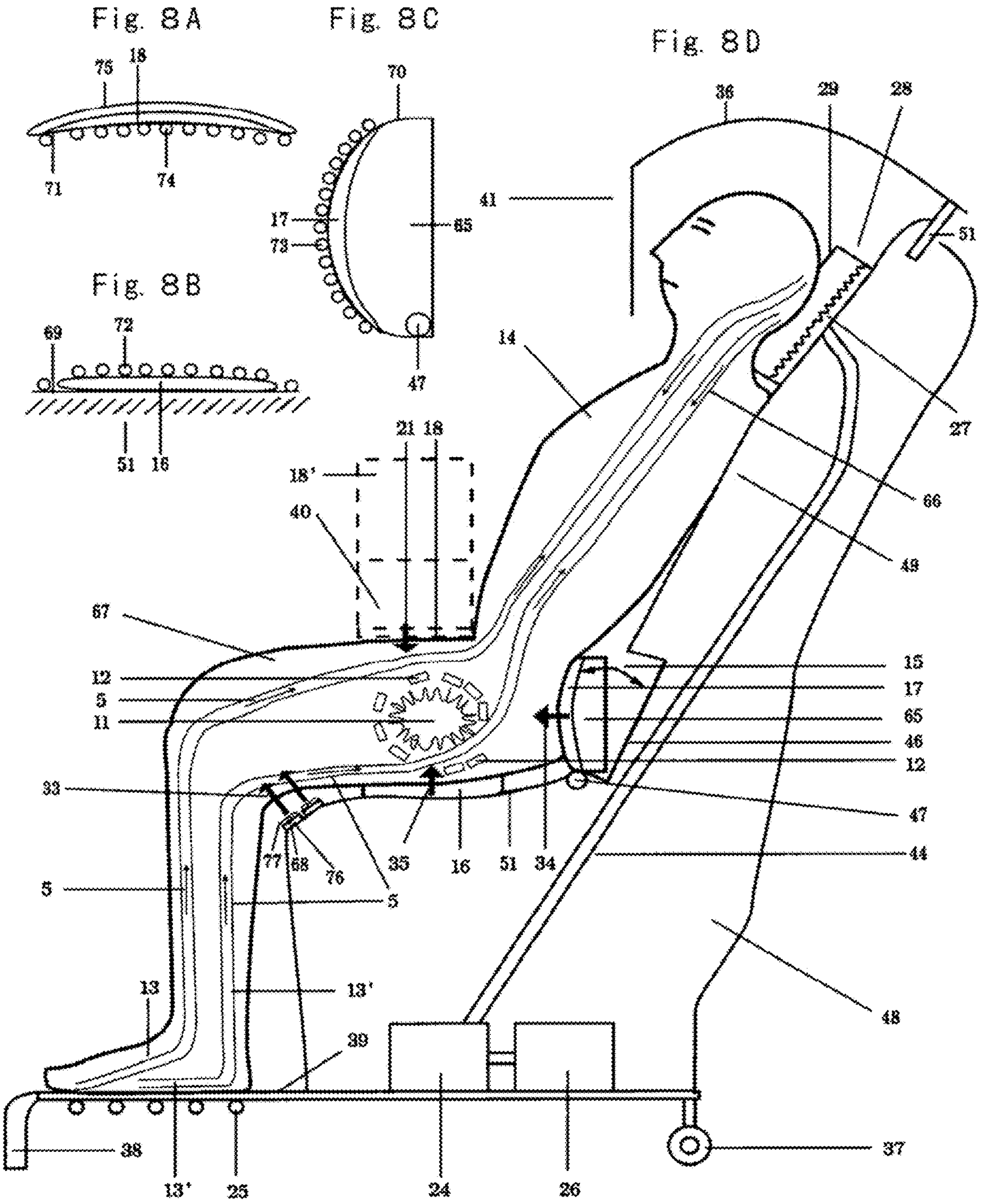

FIG. 8A shows an energy dispatcher on the abdomen, FIG. 8B shows the energy dispatcher on the buttocks, and FIG. 8C shows an energy dispatcher on the waist. FIG. 8D shows the fundamental theory of this therapy and the apparatus of the present invention, also showing a patient using the apparatus of the present invention. FIG. 8D also showing the inside of the patient (14) with affected part of ductal cancer and a principle theory of a therapy system of the present invention. In the figure, a biocompatible material (12) of the present invention is injected around the cancer (11). The injecting method was explained already in FIG. 5. (13) is a blood vessel surrounding a cancer (11), and (5) is blood flow. (39) is the present invented Feet Actuator Plate which heats feet and the blood which crime up to around the cancer, and raises the temperature of the blood (5) in the blood vessel (13) from 36° C. (body temperature) to 42° C. or more. This mechanism is to heat the feet plate (39) by condenser (25) which heat caused by compressed refrigerant, for example, Freon, which compressed by the compressor (24). The temperature of feet plate (39) was 45° C. in an actual measurement which confirmed by the present inventor.

(27) is a Head Cool Down Actuator of the present invention to cool a Mind Stabilizer of the present invention (28). (27) is cooled by the evaporator of the refrigerant that has passed through a pipe (44). (29) is the present invented rubber sheet mixed with aluminum powder. It fits a head and has good cooling thermal conductivity. As a result of the experiment by this inventor, a temperature of a surface of around head was 10 to 14° C. The reason for providing a Mind Stabilizer (28) by a Head Cool Down Actuator (27) of the present invention is that the patient cannot tolerate high temperature heating over 5 minutes. It was confirmed by an experiment of the present inventor that it is indispensable to provide a Mind Stabilizer (28) by a Head Cool Down Actuator (27) that mainly cools the head, temple, and carotid artery.

And, as it will be described later, it also has a functions to normalize scattered mind of cancer patients and to increase brain power.

(16) is a Seat Actuator, (35) is far infrared ray, (17) is a Back Waist.

Actuator, and (18) is the Belly Surface Actuator of this invention. As a result of actual experiments, these surface temperatures are 60° C., and this far-infrared rays reach more than 40 mm in the body according to an experiment by this inventor, and it was confirmed that these three rays heat strongly a heat the material of the present invention which receptive energy and emissive heat to cancer more than 42° C. by overlapping rays from three directions.

Figure 9:
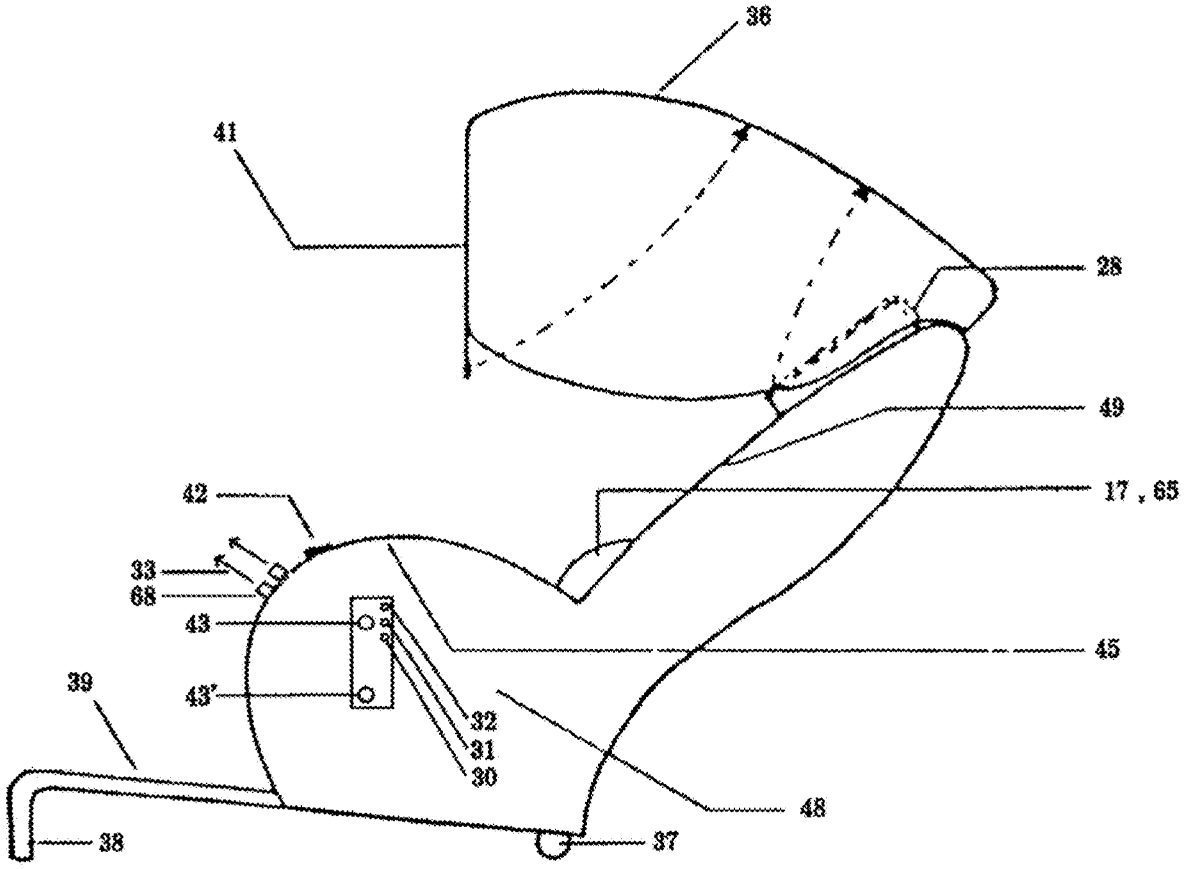
Figures 10A, 10B, 10C, 10D, 10E, 10F:
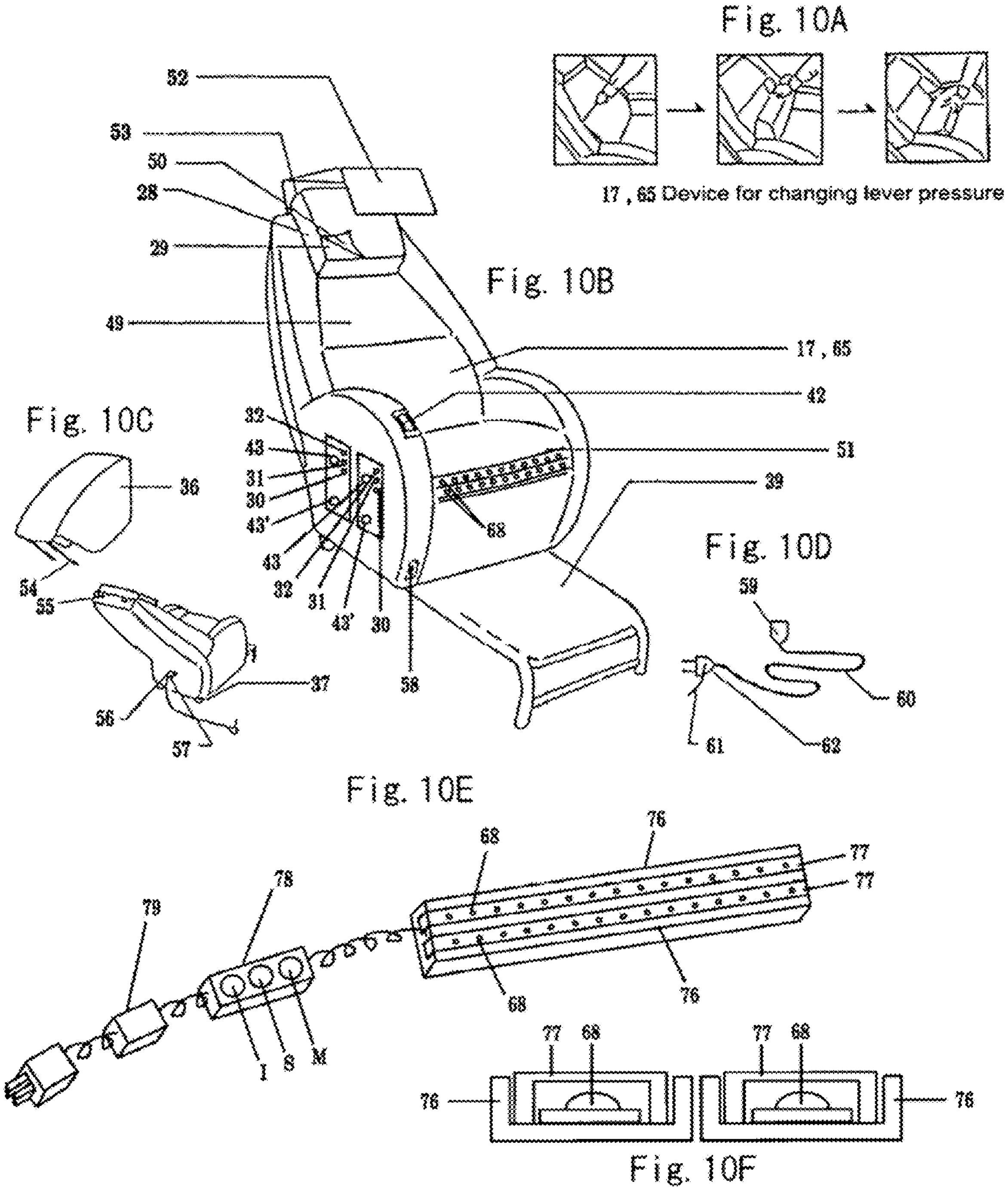

As shown in FIG. 9 and FIG. 10B, a temperature can change to low (30), medium (31), high (32) by button (43). In the actually made machine by the present inventor, the low temperature is 30° C., the medium temperature is 45° C., and the high temperature was 60° C. (43') is a power cut button. (16), (17), and (18) is not limited to the above mentioned far-infrared ray, and other energy, for example, RF, IH, ultrasonic wave, laser, microwave, THz (terahertz) including LED and other energy device are usable. These cases are also included in the present invention.

FIG. 9 is a side view of an apparatus of the present invention. FIGS. 10A-10B show a three-dimensional view of the apparatus. FIG. 10C shows the concentrator and the body, FIG. 10D shows the power cord, FIG. 10E shows the light behind the knees, and FIG. 10F shows section of 76 of FIG. 10E. (36) is the Concentrator of the present invention for the purpose of concentrating mind of a patient, (41) is a front shield for shielding to shut front view of a patient, (38) is a Front Foot to fix present invented apparatus. (37) is a Rear Wheel to move present invented apparatus. (42) is a main power switch.

First, inject to a patient the biocompatible material, which is energy receptive and heat emissive to cancer cell. Next, seat a patient (14) on the apparatus (robot) (48) of the present invention as shown in FIG. 8D, FIG. 9, and FIG. 10B. Turn on power, and operate (16), (17), (18), (29), (33), and (39). A feature of this therapeutic method and apparatus is to inject the biocompatible material of the present invention into the body and give energy from the outside. The reason why it is necessary to inject the biocompatible material beforehand in the body is to avoid a failure by public known thermal method which is a temperature of cancer down by surrounding blood which is 36° C.

Furthermore, by injecting a biocompatible material (12) which is energy receptive and heat emissive around the cancer, it receives energy emitted from outside by, for example, an apparatus of present invention, a material (12) receive energy and generates heat to the cancer from near place, so that beat cancer. Even if the temperature of the cancer is cooled with cold blood flow surrounding cancer, the heat from a biocompatible material (12) beat cancer cell at a temperature above 42° C. and eventually cancer dies.

Now explain in more detail about the therapeutic apparatus (robot) (48) of the present invention in FIGS. 8A-8D, FIG. 9, and FIGS. 10A-10F. (36) is a Concentrator of the present invention, which is a shelter cover for calming the mind of the patient (14), and (41) is a blindfold curtain which obstructs patient's visibility. To heat a cancer cell which is inside body to 42° C., it is necessary to maintain the body surface at 45° C. In order to do that, it is necessary to raise the room temperature up to 130° C. But a patient cannot tolerate such high heat.

The therapeutic apparatus of the present invention provide Seat Actuator (16) which is, for example, far infrared ray dispatcher on the seat surface. A waist pillow (65) is stored in the dent (20) on the back and goes in and out (15) around the hinge (19). A Waist Energy Actuator (17) is provided on the surface of the waist pillow (65) fitted to patient's back waist. Further, an Abdominal Energy Actuator (18) is provided at the tip end of the belt (40) ((18') is lifted position) and Abdominal Actuator (18) will wrapped around the abdomen of the patient (14) like abdomen warmer.

Additional Actuator (18) fits a body shape of a patient (14) by own weight of (18), and it responds up and down according rises or falls of belly by a patient's abdominal breathing.

A motor (26) drive compressor (24), and a refrigerant, for example, Freon is conveyed to the condenser (25) to generate heat. It heats the foot stand (39). A pipe (44) conveys a refrigerant to an evaporator (27) and cools a Top Actuator (27), which surface made of flexible head resting sheet (29) of this invention, which made of aluminum powder mixed into rubber which makes high thermal conductivity rubber. Encapsulating a patient's head put on here and cool less energy loss. This relieves suffering of patients from high temperature. The mechanism of present invented apparatus is that the blood heated and risen by the Actuator (16), (17), (18) will cool down at a brain and remove the patient's pain by (29).

An effect of healing a mind of cancer patients by cooling head will be described later. In addition, the equipment of the present invention has a lighting apparatus of back of the knee (33). This is a semiconductor light emitting diode LED tape (68) put into aluminum U case (76), which is covered with LI-shaped protective plastic cover (77). This is adhered under knees. This is connected to a power supply through a converter (79) via switch (S) (78) having mode (M), weak/strong (I). In a back of knees there is a nerve that feels a light like eyes. The lighting device (33) of the present invention which is back of knees is normalizing a brain and calming hearts of cancer patients in a staggered state by cancer.

As a result of experiments by the present inventor, the present invented apparatus improved the eyesight power up to 120% in 20 minutes. After using present invented apparatus 20 minutes, Kraepelin test resulting in an increase calculating power by 130% and improved drawing capability was confirmed by testing domestic and internationally 1000 people and more. The results of this experiment will be described in detail later with data. The above is the basic explanation of the therapeutic apparatus (robot) of the present invention.

Listing many differences between the present invention and public known therapies, the first, a very important point is to inject the biocompatible material (12), which is energy receptive from outside and emissive around cancer (11) of the patient (14), and dispatch energy from outside. The biocompatible material (12) receives energy, which emitted from the apparatus of the present invention (robot) (48). The biocompatible material (12) is heat to the cancer (11) and the peripheral blood flow (5) up to high temperature of 42° C. It heats the blood flowing around the cancer and cancer itself resulting to kill the cancer stem cells. It also increase immunity and prevent recurrence and metastasis. This is the therapy and the apparatus of the present invention.

This is the first different point from public known hyperthermia.

The reason why public known hyperthermia therapy is not effective, is that even if the cancer (11) is heated, the peripheral blood vessel (13) carries contentiously colder blood (5), so that the temperature of the cancer (11) does not rise as expected.

The second difference of the present invention from public known hyperthermia treatment method is to increase the temperature of the blood (5) flowing in the blood vessel (13) around the cancer (11) to eliminate the problem of cooling cancer by the peripheral blood flow. Thus, in addition to heating from the biocompatible material, which is energy receptive and heat emissive (12), the peripheral blood flow is also heated by the Feet Heat Actuator (39) of the present invention.

The Feet Heat Actuator (39) of the present invention is heated by the condenser tube (25) (or an electric heater) whose temperature has been increased by the compressor (24), which compress refrigerant, for example, Freon. By placing patient's feet here, the blood vessels (13), (13') of the patient's feet are heated. Since heated the blood (5) in the blood vessels (13), (13') continues to heat the surrounding cancer (11) and the biocompatible material (12), temperature of cancer (11) which cooled by cold blood flow are finally rise and cancer cell killed finally. This is the second difference of the present invention from public known hyperthermia.

The third difference from public known therapy is that the present invented apparatus has a Top Actuator that powerfully cools the patient's head. By this, the patient can withstand high heat.

The fourth difference is to calm a disturbed mind of cancer patients.

The fifth difference is increase patient's brain capability both left and right brain, such as eye sight power, calculating power, and drawing power. These details will be described later.

The sixth difference is a Top Actuator of the present invented apparatus which can cool and activate Brown Adipocytes which located in the patient's neck, shoulder blades, and armpits. The Top Actuator removes Active Fat which cancer likes, also increase Adiponectin which increase immunity.

The seventh difference from public known treatment method is that energy (16) from a Seat Energy Dispatcher (35), an energy (34) from a Lumbar Energy Dispatcher (17), and an energy (15) from an Abdominal Energy Dispatcher (18) are three-dimensionally overlapped. This makes it possible to strongly focused heat to the cancer (11) with three times higher power. It is confirmed that it is possible to kill the strongest bad face cancer by an experiment using the body of the patient. A dotted line (18') showing Abdominal Energy Dispatcher (18) lifted portion before a patient (14) sits. As mentioned above, (22) is a belt supporting Abdominal Energy Dispatcher (18). These energy dispatcher are connected to a power supply by electric wires (not shown).

Hereby explain more detail about energy dispatcher, for example, far-infrared ray pad. As shown in FIGS. 8A-8C, the reflectors of energy (69), (70), (71) are made of aluminum or a silver color sheet are attached under the energy dispatcher (16), (17), (18). Heat resistant nets (72), (73), (74) are stretched thereon, and the energy dispatcher, for example, far infrared heater pad (16), (17), (18) are inserted therein. Because of this structure, it is possible to replace the energy dispatcher (16), (17), (18) to other energy dispatcher, for example, RH, LED. The nets (72), (73), (74) are heat resistant and are materials that allow the energy (21), (34), (35) to pass through.

A Waist Actuator (17) is curved along the back waist and the lumbar pillar (65) is moved around the pivot (47) so as to match the angle of the patient's back waist. (75) is an extension of the belt (40) to support energy dispatcher, for example, the far infrared heater pad (18). It is flexible so that it can respond to the shape of the patient's belly. Because a heat reflector (71) made of aluminum or the like located of bottom surface of the energy dispatcher (18), cancer cells are three-dimensionally heated by (16), (17), (18), and a therapeutic effect is maximized.

In FIG. 9 and FIG. 10B, (43) is energy, for example, far infrared ray intensity change button. It is switched to weak (41° C.), medium (40 to 44° C.), strong (45 to 50° C.) and displayed by LED (30), (31) and (32). (43') is an off button. It start effects 5 minutes at strong switch, and 20 minutes at medium switch according the actually made apparatus by the present inventor.

The eighth difference from the public known treatment method is that a present invented apparatus (robot) that makes the patient's posture Z-shaped. Public known hyperthermia treats patients laying down flat, but the apparatus of the present invention makes patients Z-shaped. This make a patient's feet sole, are horizontal to heat by Feet Heat Actuator. A buttocks, a waist and a abdomen are also horizontal by laid down (A cistern is kept horizontally and it raise and down according to abdominal breathing). On the contrary, the waist is standing—this is this posture. By this posture energy, for example, heat rays comes from three dimensions. Unlike public known treatment method, by the apparatus of this invention the patient take a posture to raise upper body and head (so that a head can be cooled and a patient can withstand high heating).

The ninth, which is different from public known treatment method, is that "heating of a cisterna chyli can be done while lying down". The cistern is a reservoir for lymph, but it does not work unless stimulated. The energy emitted from the buttocks, waist, and belly overlap three-dimensionally and is sent to the chin bath, the internal lymphs become active, NT cells, T cells, and killer cells which attack cancer. By flattening the belly part of the patient by the present invention, the cistern is also leveled, so that the immunity in it is activated.

The tenth difference from public known treatment method, the present invention does not require constraint, and Abdomen Energy Dispatcher freely rises and falls on the patient's belly. Thus, after 2 hours from meal, when a nutrient arrives in a cistern, even if a patient stretches a belly with abdominal breathing, it can follow it. Also, since a belly and to energy dispatcher are in close contact with each other at any time, therefore there is no energy loss and an immunity can be effectively increased.

As noted earlier, 2 hours after a meal, the cistern is activated by abdominal breathing, and immunity is increased. In addition, abdominal respiration reduces the stress of a patient and further enhances a therapeutic effect, which is for superior than public known therapy.

The eleventh and very important point, which is different from public known treatment method is stabilize scattered minds of cancer patients. When a cancer is declared to patient from doctor, a patient's heart is scattered by a fear of death, and it is reported that rich patient buys a lot of underwear, rich patient buy expensive car such as Lamborghini. The present invention can calm down a scattered heart of a cancer patient. A Mind Stabilizer (28) activated by a Top Actuator (27) the Feet Actuator (39), Concentrator (36), and Knee-Back LED Irradiater (68) of the present invention are effectively multiplied to stabilize and normalize a brain condition.

The twelfth difference from the public known treatment method is the Knee-Back LED Illuminator (68) which is also an intra-cerebral adjustment apparatus of the present invention. This will be explained in more detail.

A detail drawing of the Knee-Back LED Illuminator is shown in FIGS. 10E and 10F. The Knee-Back Illuminator (68) of the present invention is illuminate (33) an inside of the knee (67) of the patient (14) by light, for example, LED. 100 V power supply to LED (68) through the converter (79). Connecting made switch (78), LED light—irradiate state can be changed, such as M (mode) I (intensity) and S (comfort) (shown in FIGS. 10E and 10F). The light is for brightness and a case where a light other than LED is also included in this invention. It is known that there is a visual nerve same as eye exist back. By lighting this point, a brain of cancer patient (14) calm down to normal who was shocked, disappointed by fear of death. It is public known that in case of jet lag in overseas business trip, body clock is adjusted by looking at sun or a very bright light. This apparatus uses this principle, but difference is that light is applied to a back of the knee instead of the eyes. The therapeutic apparatus of present invention is not only normalizes a distorted state of a cancer patient's brain but also calms disturbed mind from a back of knee.

Figure 32:
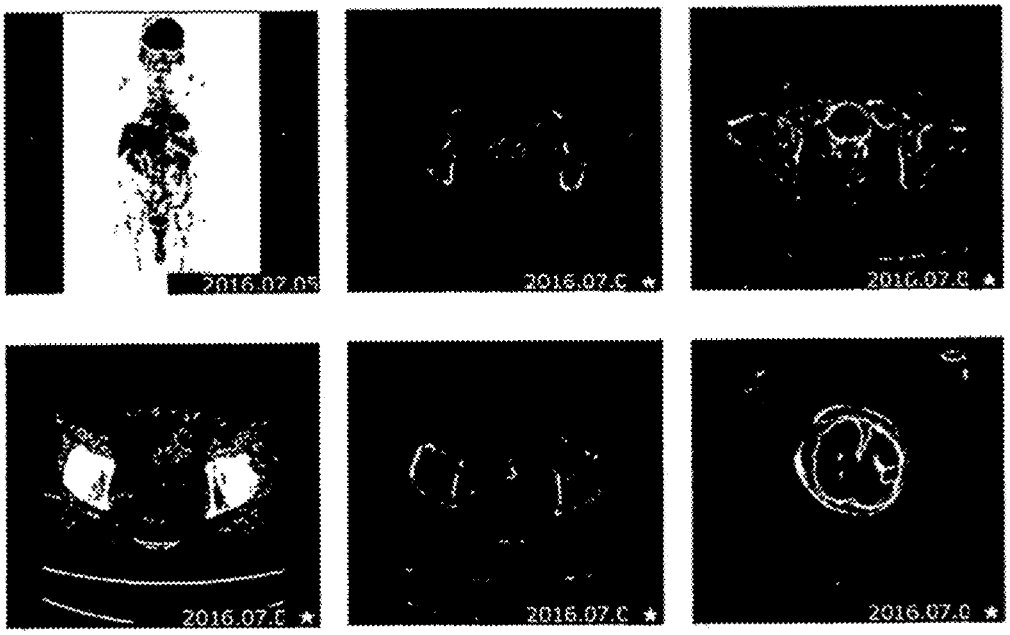

The thirteenth difference from public known treatment method is that effective treatment can be done for cancer bone metastasis without side effects. The present inventor found cancer and promptly started treatment. However, when examined with PET/CT and MRI, it turned out that FDG accumulation was on the right pelvis of the right sciatica. It is at the upper right end out of six images in FIG. 32.

FIG. 33 shows NM examination report for this image, stating that this is metastasis.

FIG. 34 shows the image diagnosis report, which shows that the cancer has disappeared by the present invention.

Even if it is not metastasis, radiation irradiation during cancer treatment causes bone infarction (osteonecrosis).

Metastatic bone tumors, makes bone fragile, pain, pathological fractures, metastasis to the spine and paralysis of the dorsal marrow. It also causes pain due to cancer cytokine stimulation, PH lowering stimulation and nerve compression of dorsal marrow. Normal bone has a good balance of osteoclasts and osteoblasts, but metastasis to bone destroys this balance, osteoclasts are activated, bone melts and becomes brittle. In the case of ductal cancer—the inventor's case—, on the contrary, the function of osteoblasts is increased, abnormally many bones are made, and it is easy to break.

Public known treatments combine chemo, surgery and radiation. For pain, use morphine and others.

Zoledronate (trade name: Zometa), a conventional bisphosphonate drug formulation, has been converted from what was used for rust removal of iron pipes, and has side effects. Necrosis of the chin bone has been reported.

Also, hormonal therapy, which is a public known therapy, revives pain due to hormone resistance.

Public known surgical therapy is highly invasive and dangerous. Even if public known radiotherapy can take pain, cancer itself can not be killed, and radiation causes injury to surrounding internal organs such as a intestines.

If bone metastasis is left untreated, become brittle bone. Also, if it metastasizes to bone marrow, it becomes fatal.

The treatment by this invention is also effective against this difficult bone metastasis. The theory of therapy for bone metastasis of the present invention will be explained.

Figure 36:
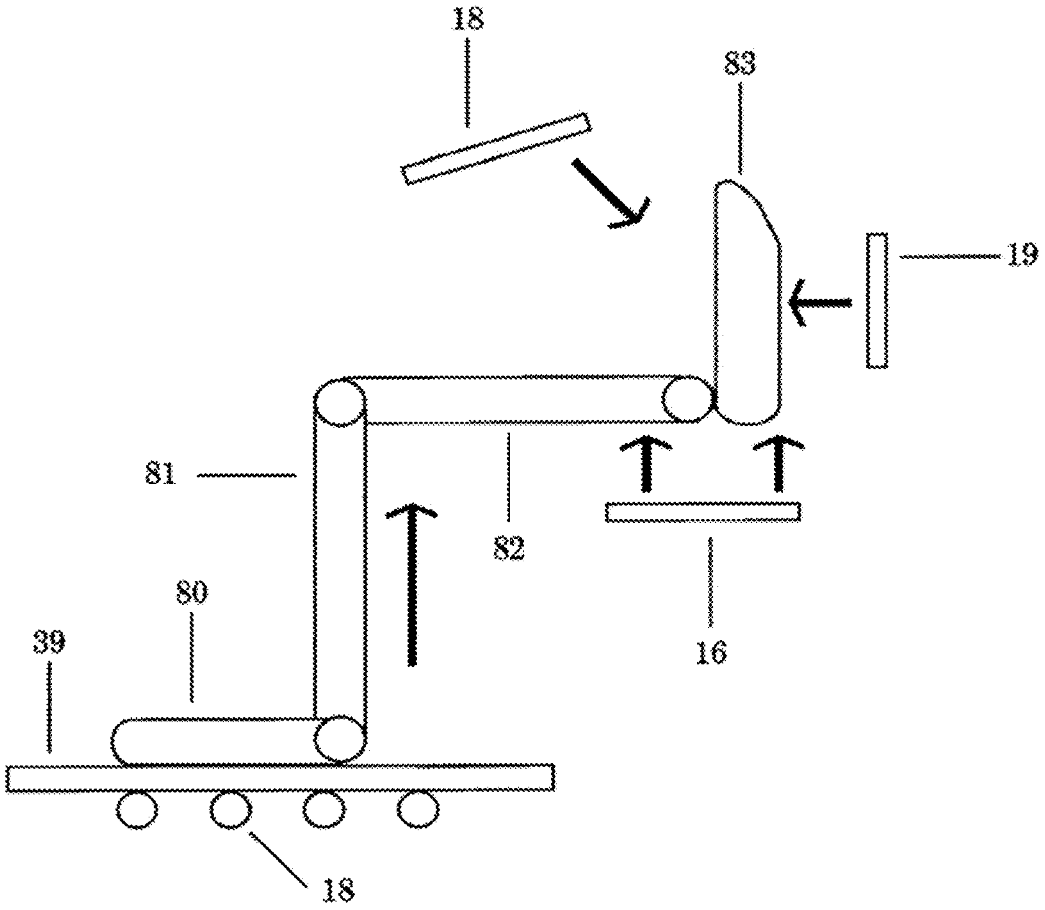

FIG. 35 shows the characteristics of biological materials, among which the thermal conductivity of bone is 2.208, which is much better than the other parts of the living body. The present invention utilizes this thermal conductivity. As shown in FIG. 8D and FIG. 36, when the feet bone (80) are placed on the feet plate (39) heated by the heater (25), this heat is transmitted to the knee bone (81). Thereafter, via the femur (82), the sciatic and pelvis (83) are heated to 42° C. In addition to the foot bone (80), the sciatic and pelvis (83) are strongly heated to 42° C. from the energy dispatcher (16), (17), and (18), for example, far infrared rays, microwave heater to kill the cancer.

Figure 37:
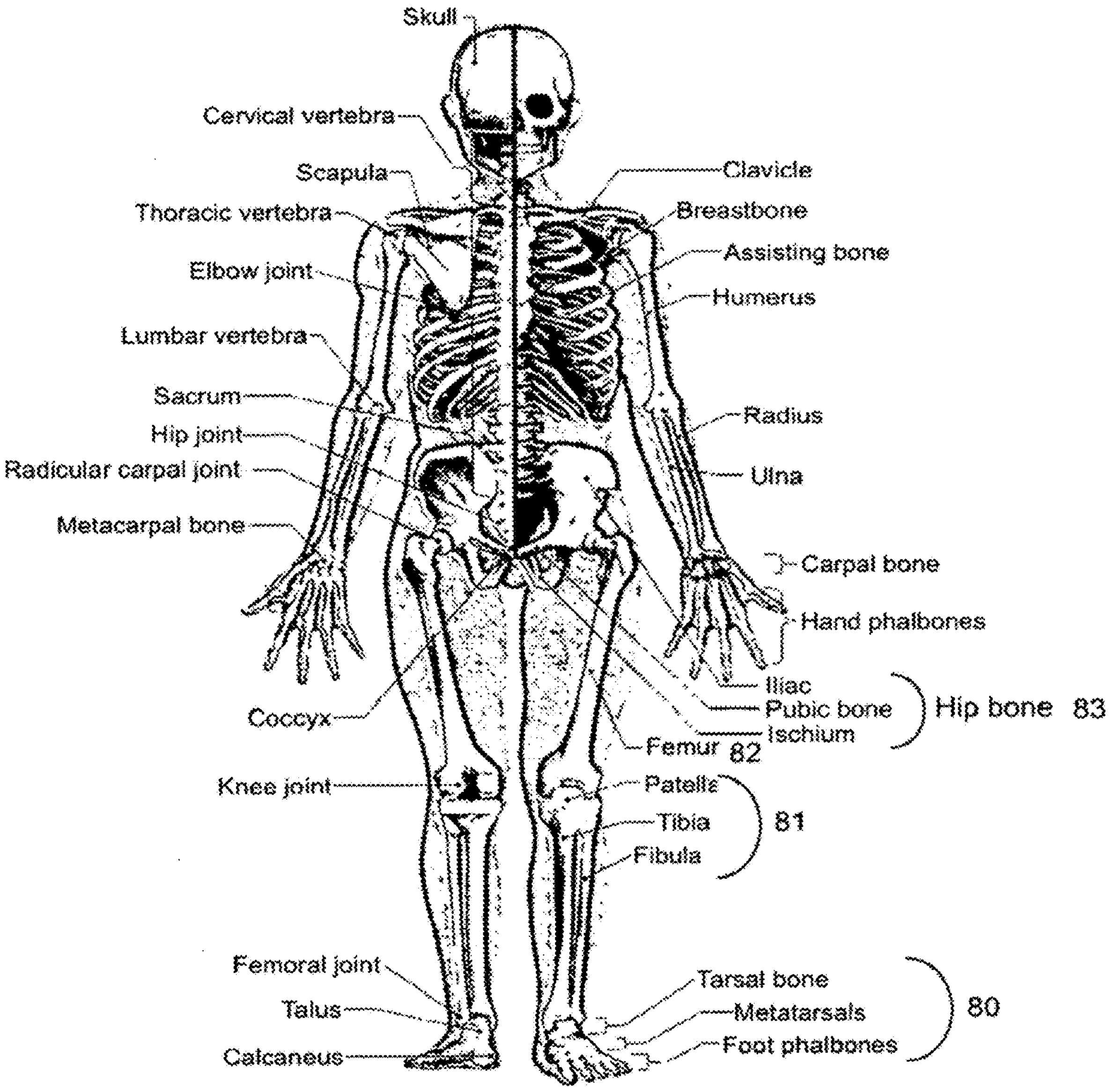

FIG. 37 is a human structure figure for explaining a bones described above.

Fourteenth difference from public known treatment method, that the present invention is effective without side effects for another cancer, for example, chest and back, breast cancer, lung cancer, pancreatic cancer, liver cancer.

Figure 38:
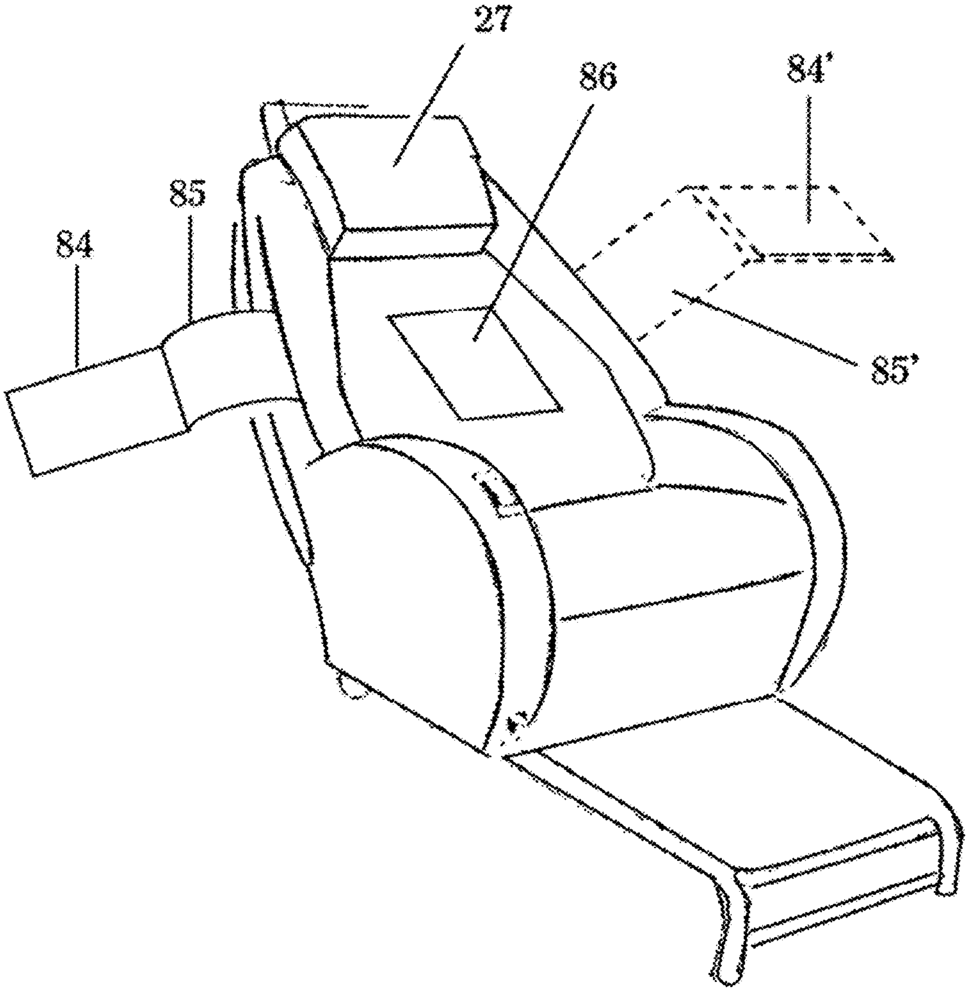

FIG. 38 shows an apparatus of the present invention for these diseases. Although the principle is the same as in FIGS. 8A-8D, an energy dispatcher (17), for example, far infrared rays, microwave, 13.56 MHz radio wave, LED is provided at the back in a vertically long shape (86) instead of the waist part (17) as shown in FIG. 38. In addition, it is also provided energy dispatcher (84) on the chest in the horizontal direction, instead of abdominal position (18) of FIG. 8A. (85) is a belt to hold (84). The length of (85) is longer the better, because the range where (84) can be placed extend to the breast and the axillary lymph nodes (armpit lymph).

In the case of left breast cancer, which has many cases, provide (84), (85) on the left side, because it becomes easier to cover a left armpit with (84) as indicated by (84) and (85) of FIG. 38. In a case of right breast cancer, (84') and (85') are provided on a right side as shown by a dotted line. Also, instead of fixing 85, by attaching it by velcro, 85 and 84 can be placed anywhere according to a position of a cancer, so versatility is enhanced.

Figure 39:
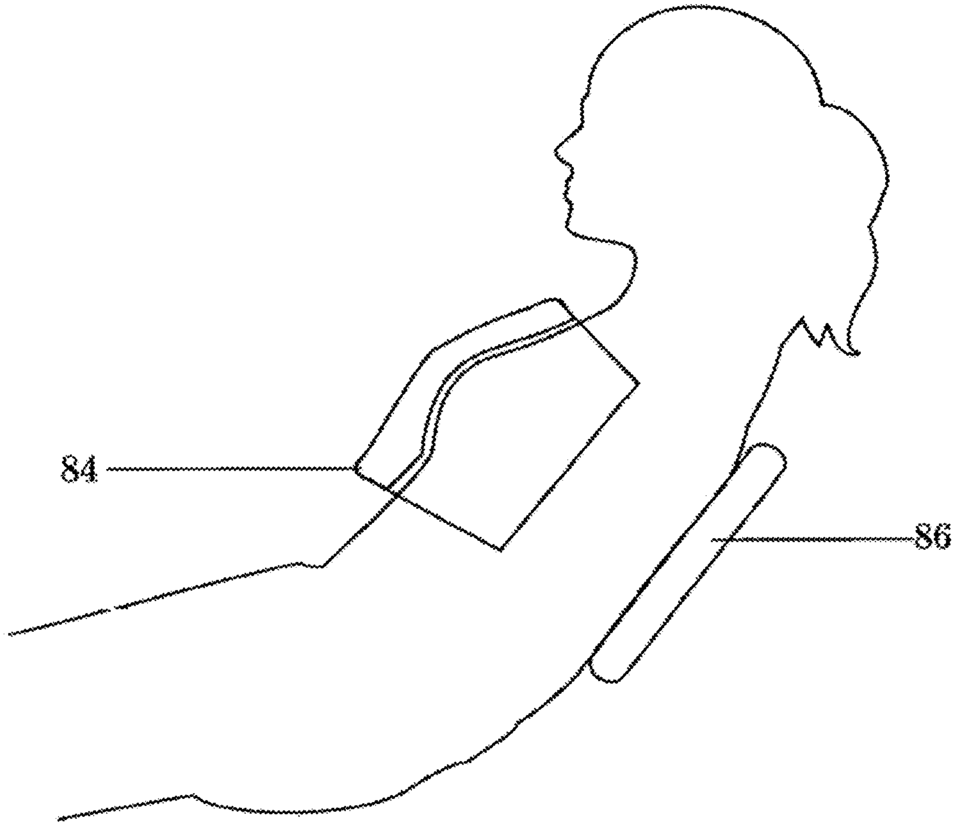

FIG. 39 is a side view of the patient (14) using the apparatus of the present invention.

The fifteenth difference from the public known therapies, the present invention can treat cancers that have spread to various parts. As mentioned above, the therapy of the present invention activates immunity to attack cancer. Injecting a chemical that generate heat by light and above chemical combines to antibodies which has character to adhere to regulatory T cells (Cancer cell use "regulatory T cells" to suppress immunity, and are skillfully escaping from immune cells that attack cancer cells). After injecting to the above chemical to cancer patients, for example, with lung cancer, colorectal cancer make a patient lay down on an apparatus of the present invention, and shoot energy, for example, near infrared ray, LED from device (17) in FIGS. 8A-8D. By heating the above chemical, regulatory T cells around the cancer killed. As a result, cancer cells cannot escape from the attack of immune cells and die. The above therapy is also included in the present invention.

Experiments confirmed that cancer cells in the area not hit by energy, for example, near-infrared ray dispatcher (17) are also shrinks.

The reason for this is, it is believed that attacking the cancer immune cells are moving inside the body. In other words, the therapy of the present invention is effective for cancer that has metastasized.

The head cooling device of the present invention is, as described with reference to FIG. 8D, an occipital region is cooled by a Top Actuator (27).

Figure 40:
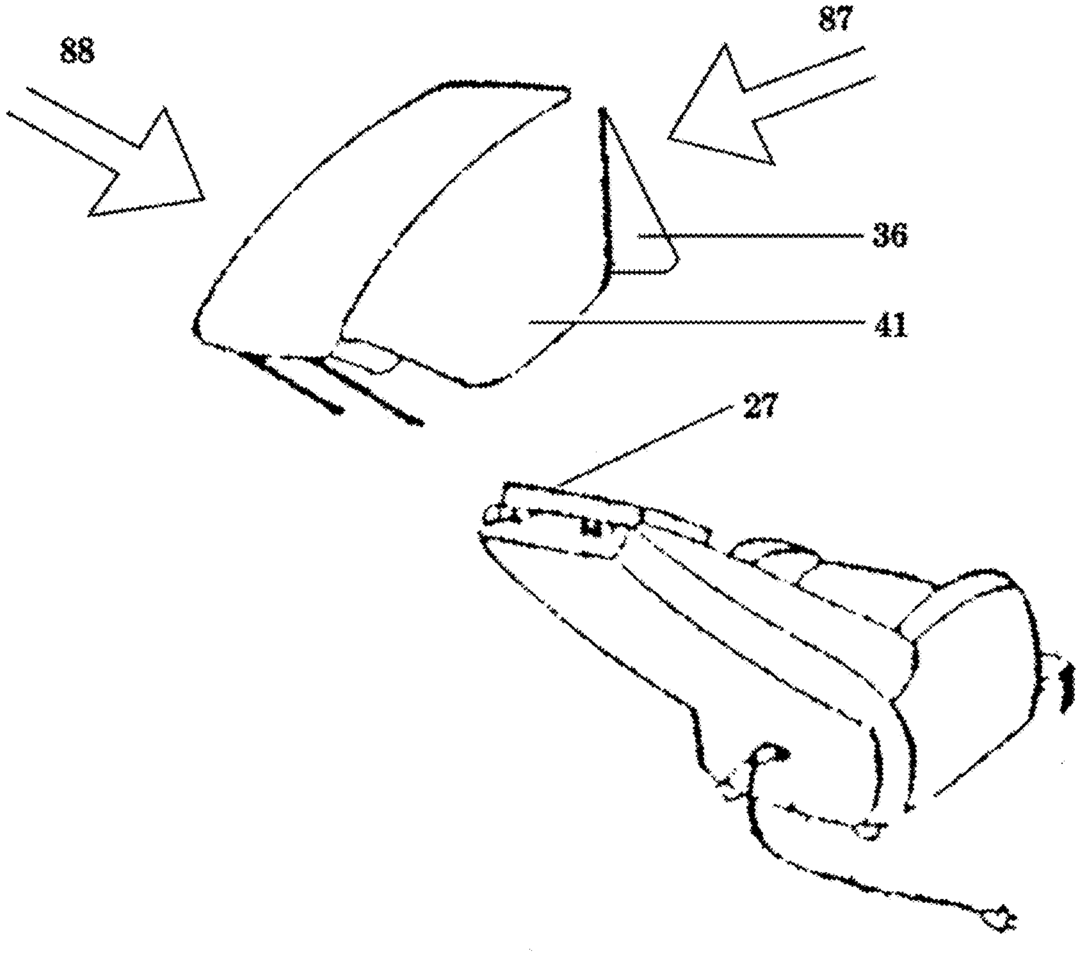

FIG. 40 is an explanatory view of cooling the forehead and face by combination with a Concentrator (41).

As shown in FIG. 40, when a cooling air (87) of a room air conditioner is coming from front cold air accumulated in a Concentrator (41), by lifting up a front shield (41), so that cool a forehead and face.

Also, when a direction of an air conditioner in a room comes from a side (88), by raising a shield of a side of a side of Concentrator (41) where cold air of air conditioner is coming, and closing other side and the front shields (36) of a Concentrator (41) are lowered, so that cold air is filled in a Concentrator (41) to cool a frontal head and a face. As described with reference to FIG. 8D, since a Top Actuator (27) cools the occipital region, the entire head is cooled from front and back. Thus, the apparatus of the present invention can alleviate the patient's pain caused by high heating.

FIG. 41 shows the in vivo heat transfer equation of the apparatus of the present invention. This is a theoretical equation of this invention of FIGS. 8A-8D and FIG. 35. It can be applied to multiple layers, for example, Viscera layer, bone layer, muscle layer and fat layer. The left side of this equation is the heat storage term of the tissue per unit volume. The first term on the right side is the temperature diffusion term. The second term is the advection term by the heat quantity of the arterial blood flowing into the tissue. Third and fourth terms represent heat transfer between arterial system vasculature, venous system vessel and tissue, respectively. The fifth term is the heat generation term.

The lower equation in FIG. 41 shows the heat conduction equation for the arterial system and the venous system. This is the equation concerning the heat transfer of the blood (5) around cancer heated by the feet Heating Table (39) and an equation of a heat transfer of a blood (66) of the head cooled by The Top Actuator (27) and the Concentrator (41).

The present inventor conducted experiments to ascertain whether the therapy method and the apparatus of the present invention really have the above-mentioned effects by using the present inventor's own body which has cancer.

Figure 11:
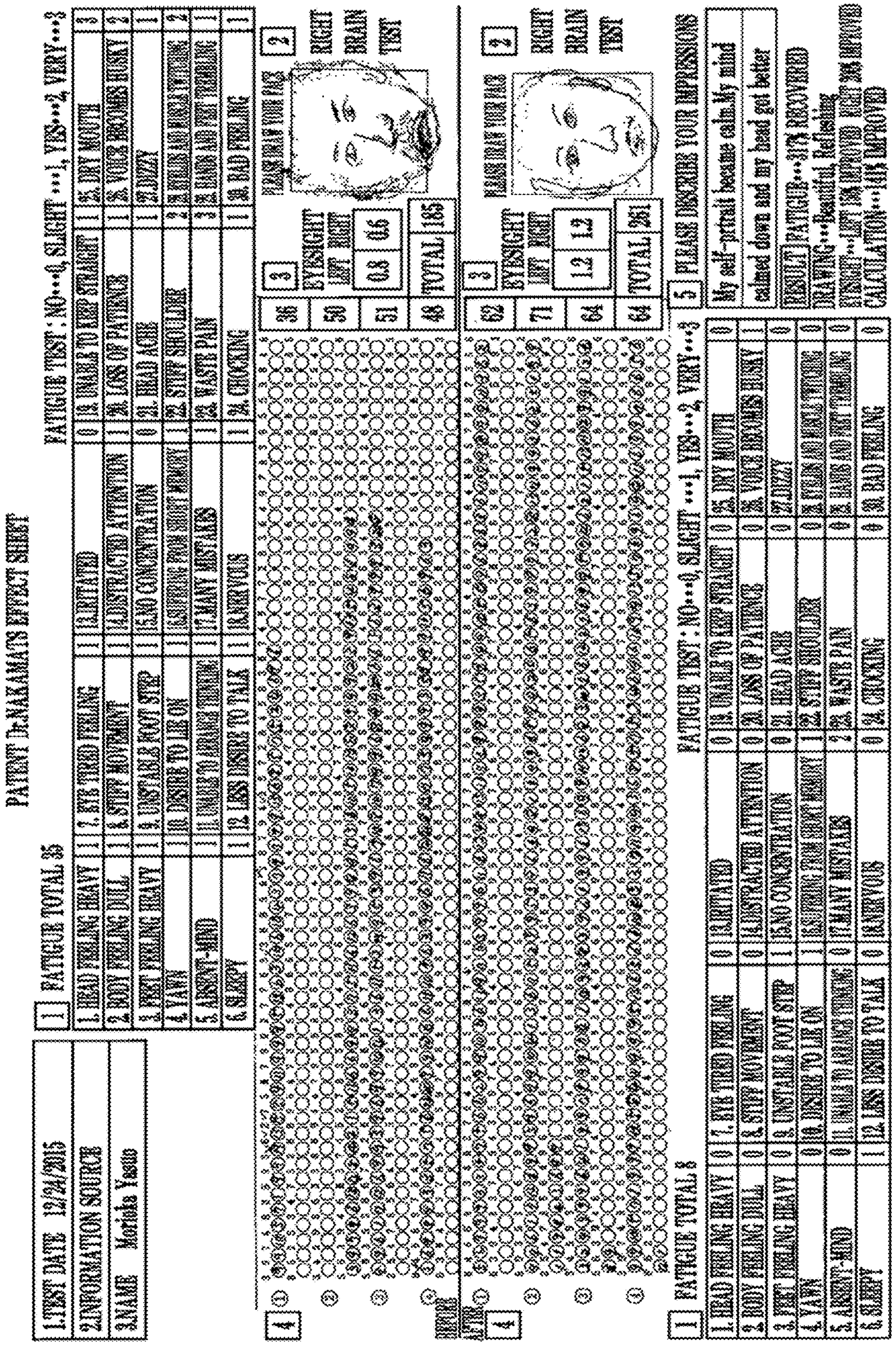

In FIG. 11, from a center line to a left (a top when FIG. 11 placed horizontally) are results of a Kraepelin test, a fatigue test, an eye sight power test and the drawing test before the patient uses the apparatus of this invention. In FIG. 11, from a center line to a right is a result of a same test after the patient has used and apparatus of this invention for 20 minutes (Questionnaires on the Kraepelin test have been changed because not to rely on previous memory). Comparing the above two, the calculation power has increased by 141%, the drawing power has also increased significantly, and fatigue has been drastically reduced from 35 to 8 by using the apparatus of this invention are proved experimentally.

Thus experiment participants reported that "the expression of self-portrait became calm, my mind settled and the activity of my brain got faster". Normalizing a scattered brain of a cancer patient is the thirteenth advantage of the present invention which is different from public known therapy.

FIG. 12 shows the result of Russian Americans using the apparatus of the present invention in New York. An eyesight power increased 250%, the memory power increased 200%.

FIG. 13 shows a result of Italian-American in New York using the apparatus of the present invention. The calculation power improved by 148%, eye sight power improved 250%, flicker test improved 346%, fatigue test reduced 400% and memory power test improved 105%.

FIG. 14 shows a test of the All Godelic who is Cuban embassy science attache using the apparatus of the present invention. As a result, a calculation power increased 139%, eyesight power left eye improved from 1.5 to 2.0, and right eye improved from 1.5 to 2.0. Also, self-portrait improved significantly.

FIG. 15 shows a result of testing of Japanese woman, a calculation power increased 134%, eyesight power left eye 0.2 was improved to 0.4, right eye 0.5 was improved to 0.6, and self-portrait drawing power increased.

Figure 16:
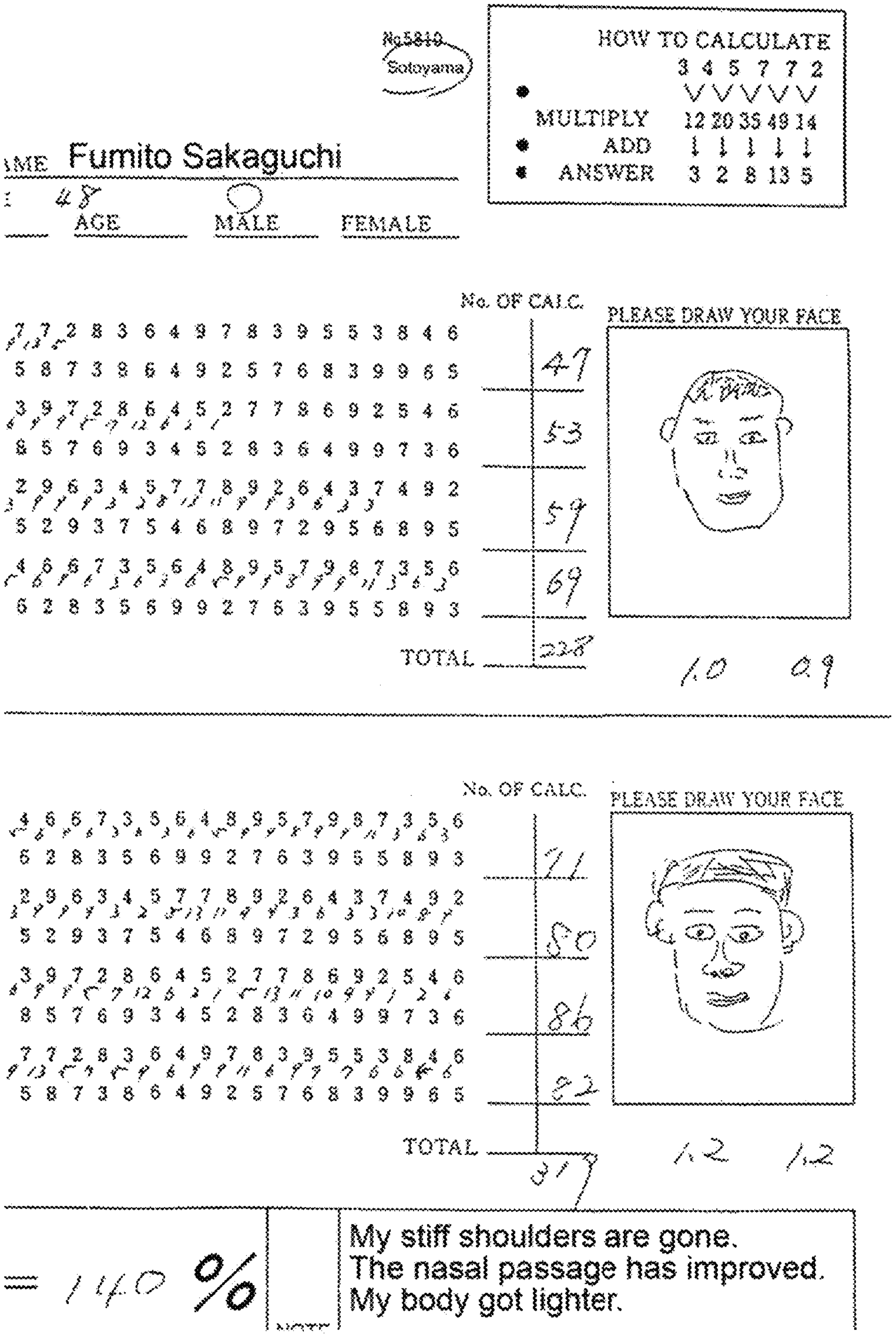

FIG. 16 shows a result of testing of Japanese man, a calculation power increased 140%, an eyesight power left eye 1.0 was improved to 1.2, right eyes 0.9 was improved to 1.2. Drawing power also improved. He reported "I have less shoulder stiffness, I feel easier breathing opened the nasal passages. I think that my body got lighter."

FIG. 17 shows the experimental result that the degree of fatigue drops from 7 to 4 after using the equipment of this invention for 20 minutes, and calculation power is increased 140%. Eye sight power increased from 0.7 to 0.9 for left eye, 0.8 to 0.9 for right eye, drawing power also improved vitality. He has reported "Relaxing and very pleasant!"

Figure 18:
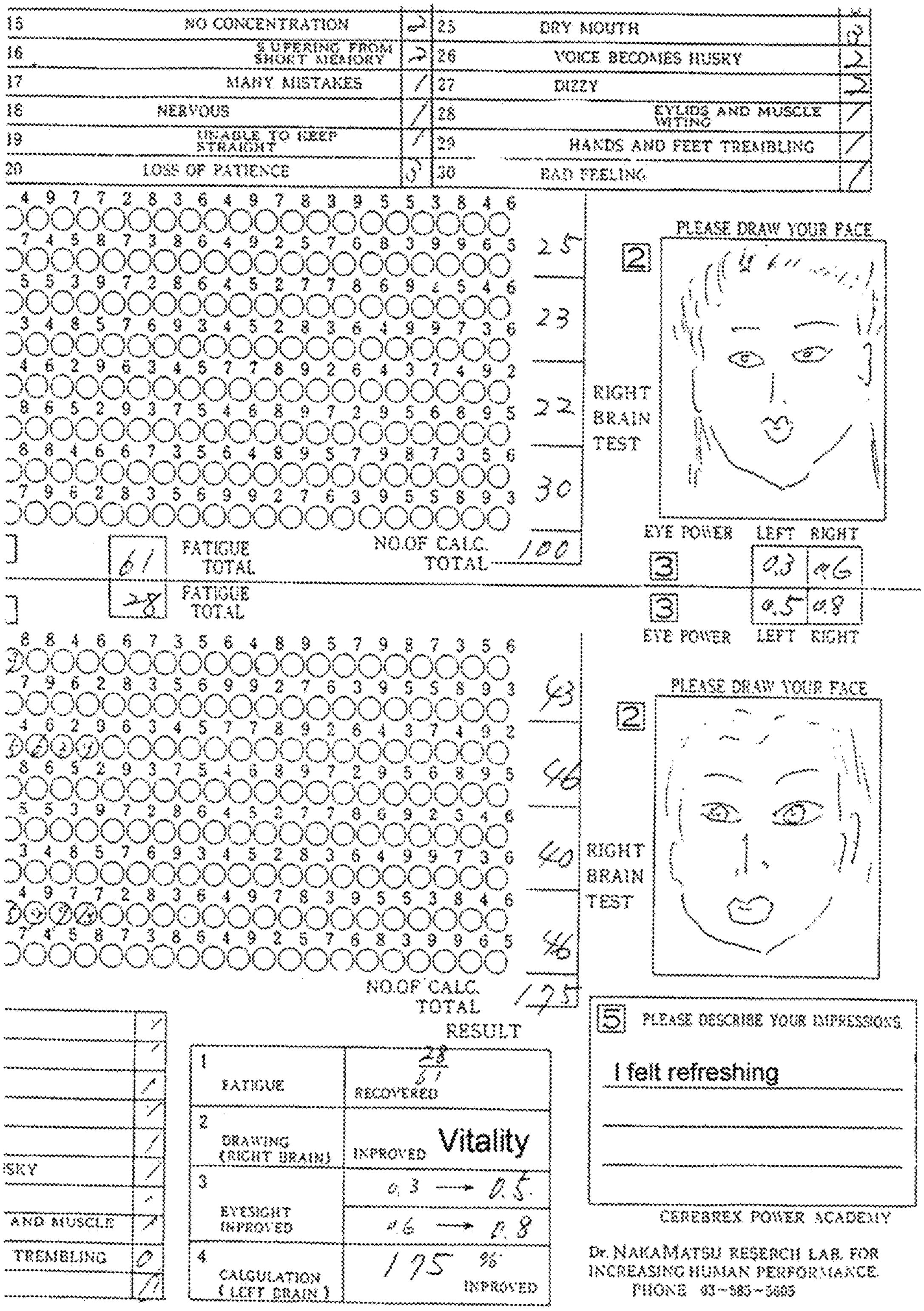

In an example of FIG. 18, a degree of fatigue has decreased from 61 to 28, a drawing power is full of vitality, eye sight power increased from 0.3 to 0.5 for left eye, 0.6 to 0.8 for right eye, calculation power has increased by 175%. He has reported "I felt refreshed."

FIG. 19 is experiment shows the fatigue decreased from 14 to 2, the drawing power of a right brain became vigorous. As for eye sight power, a left eye increased from 0.8 to 1.5, a right eye increased from 1.0 to 1.5, a left brain's calculation power increased 155%, this patient said "Wonderful feeling."

Figure 20:
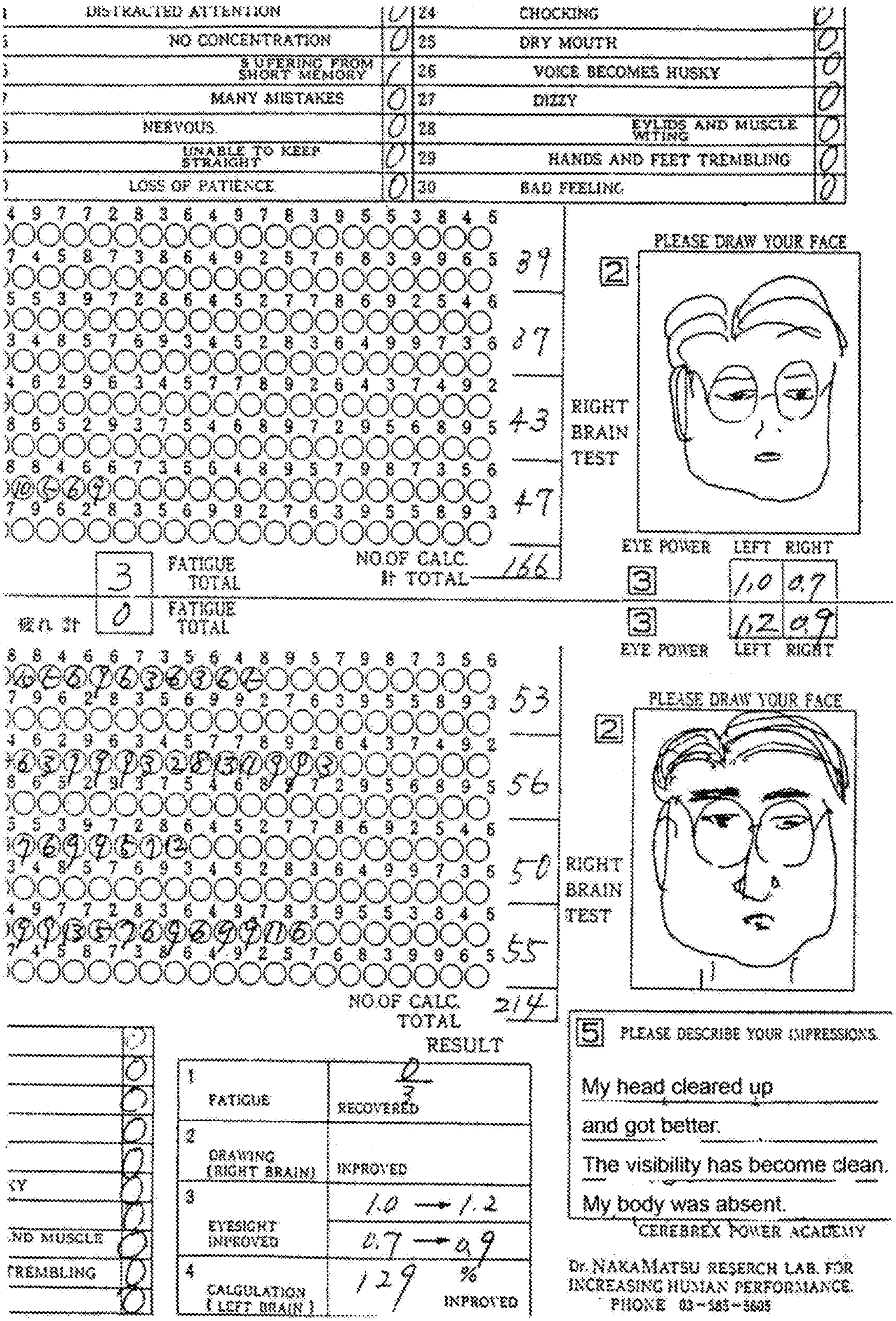

FIG. 20, shows a degree of fatigue recovered from 3 to 0, eyesight power has increased from 1.0 to 1.2 for left eye and 0.7 to 0.9 for right eye. A condition of back brain improved and calculating power of left brain is increased 129%, Patient reported "My head become clear and smart, all things looks beautiful, my body has rests."

FIG. 21 shows two cases tested at the Japan Internal Visual Academic Society, a fatigue decreased 17→0, 11→0 which prove that equipment of this invention is effective.

The above are just a few examples of a large number of clinical trials conducted by the present inventor to ascertain whether the equipment of this invention is effective. In addition to these, experimental verification was carried out at third party institutions, for example, at The Jikei University Hospital, St. Marianna University School of Medicine, Japan Medical Association, whether the therapy and apparatus of the present invention is really effective.

Among third party institutions, University of Tsukuba, School of Exercise Physiology was particularly experimentally verified studiously. This report of the University of Tsukuba is as follows.

Figure 22:
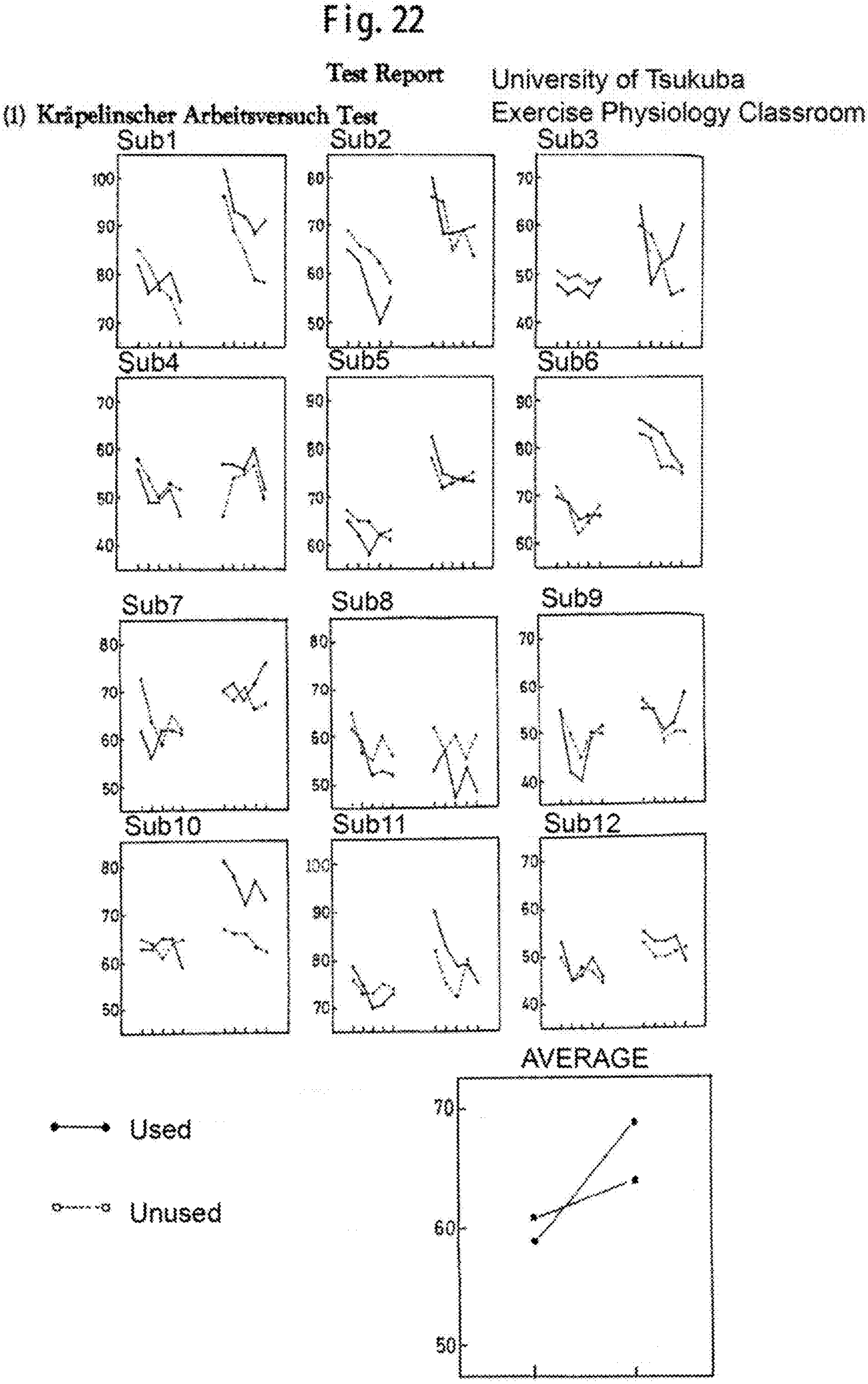

FIG. 22 shows the Test Report of University of Tsukuba, School of Exercise Physiology of the Kraepelin test using the apparatus of the present invention. It was proved that a state of a brain of a patient improved from 60 to 70 and a calculation power increased compared with a case where it was not used the present invention.

FIG. 23 is a variance analysis table for the results of Kraepelin test. The report of University of Tsukuba is as follows.

Figure 24:
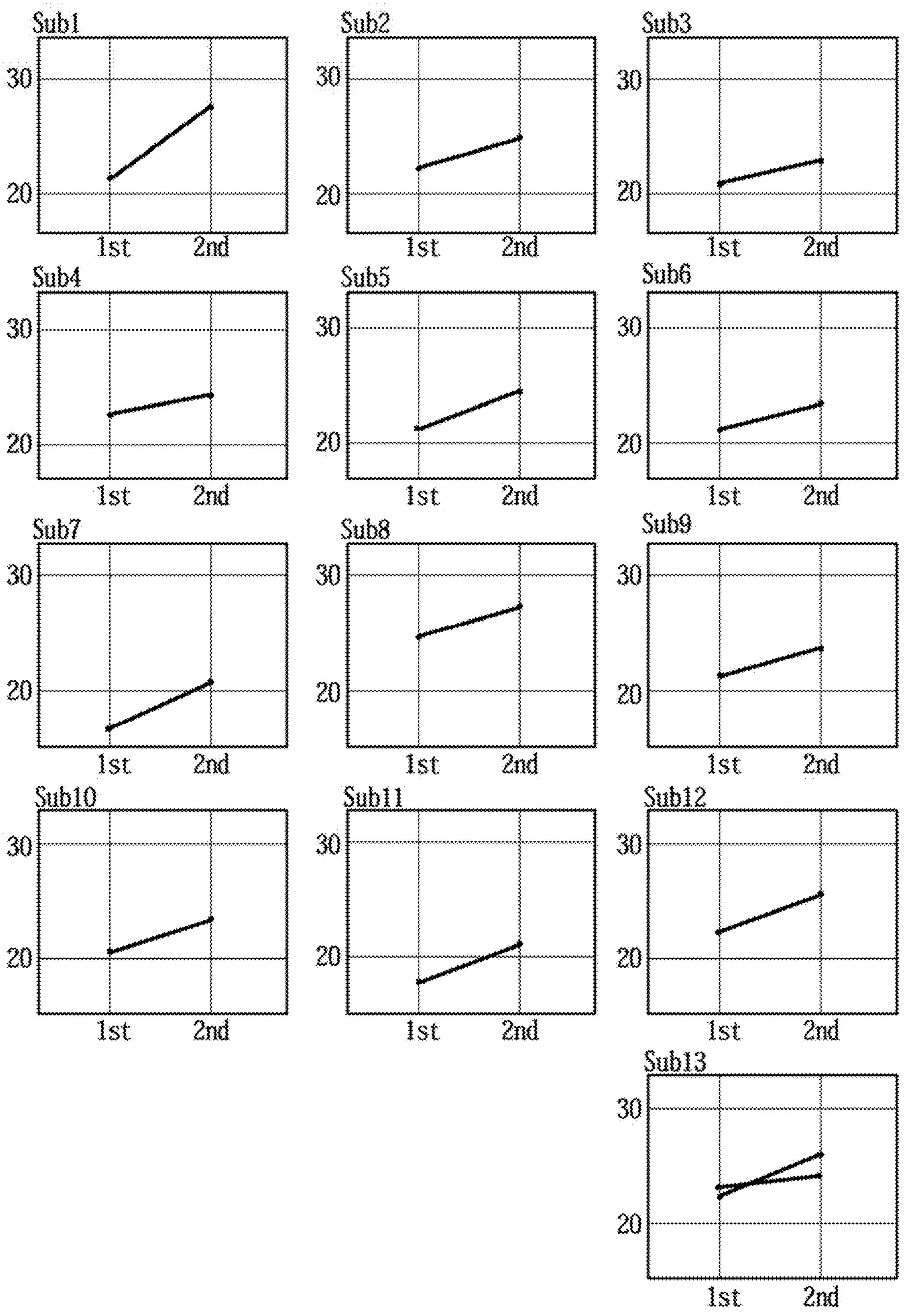

"First, we University of Tsukuba will describe the results of the Kraepelin test, and second we will describe the results of the flicker test. FIG. 1 in FIG. 22 shows the results of the Kraepelin test for each patient. In each graph, the vertical axis shows the score of the Kraepelin test. As shown in these figures, although the degree of effect is quite different depending on patient, in many cases, the performance is better in the case of using "Dr. NakaMats Invention Apparatus" than in the case where it is not. FIG. 2 on the bottom of FIG. 22 shows an average of all subjects in 5-minute Kraepelin test. As shown here, by using "Dr. NakaMats Invention Apparatus" has a bigger improvement in performance than when it is not. FIG. 23 shows results distribution table of Kraepelin test, which proves an effect of the apparatus of this invention. Next, we will describe results of a flicker test. FIG. 3 in FIG. 24 shows results of a flicker test for each patient. In each graph, vertical axis shows a frequency of threshold value possible to discriminate flick of flicker, and horizontal axis shows a case of using "Dr. NakaMats invention Apparatus" and when not using it. Two points of Dr. NakaMats apparatus using or not using are connected by a straight line to show a difference.

Table 2 in FIG. 25 is a distribution analysis chart of results of a flicker test. From this result, University of Tsukuba, school of Exercise Physiology reported "It is recognized that using of Dr. NakaMats Invention Apparatus improves flicker discrimination rather than not using".

Figure 26:
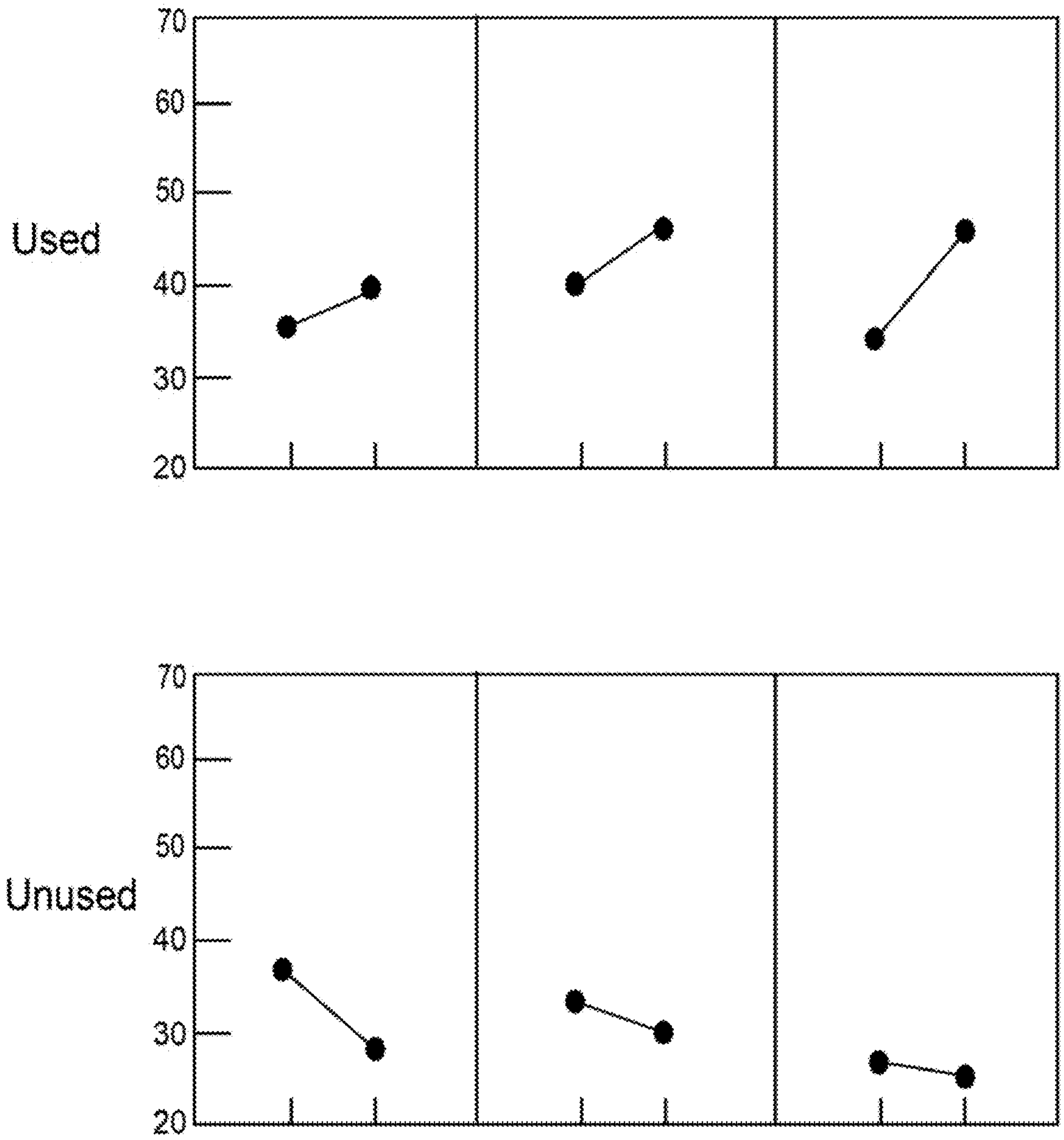

FIG. 26 shows the results of measurement of Alpha wave amount of a frontal lobe cerebral using the apparatus of the present invention (upper data of FIG. 26) and not using (lower data of FIG. 26). The conclusion of The University of Tsukuba Report is as follows: "From the above results, it is suggested that when using the equipment of this invention, a calculation thinking activity is improved 30% according to the Kraepelin test is compared with not using the apparatus of the present invention. It also suggests that a discriminatory cognitive activity is also improved by using the apparatus of the present invention to test by a flicker test". Also, University of Tsukuba which is the national university confirmed" as shown in FIG. 26, it was confirmed that Alpha wave amount in a forehead was clearly increased by electroencephalogram examination after a treatment by the equipment of this invention." Therefore, it proved that a scattered brain of a cancer patient recovered and improved beyond normal by the equipment of the present invention.

Figure 28:
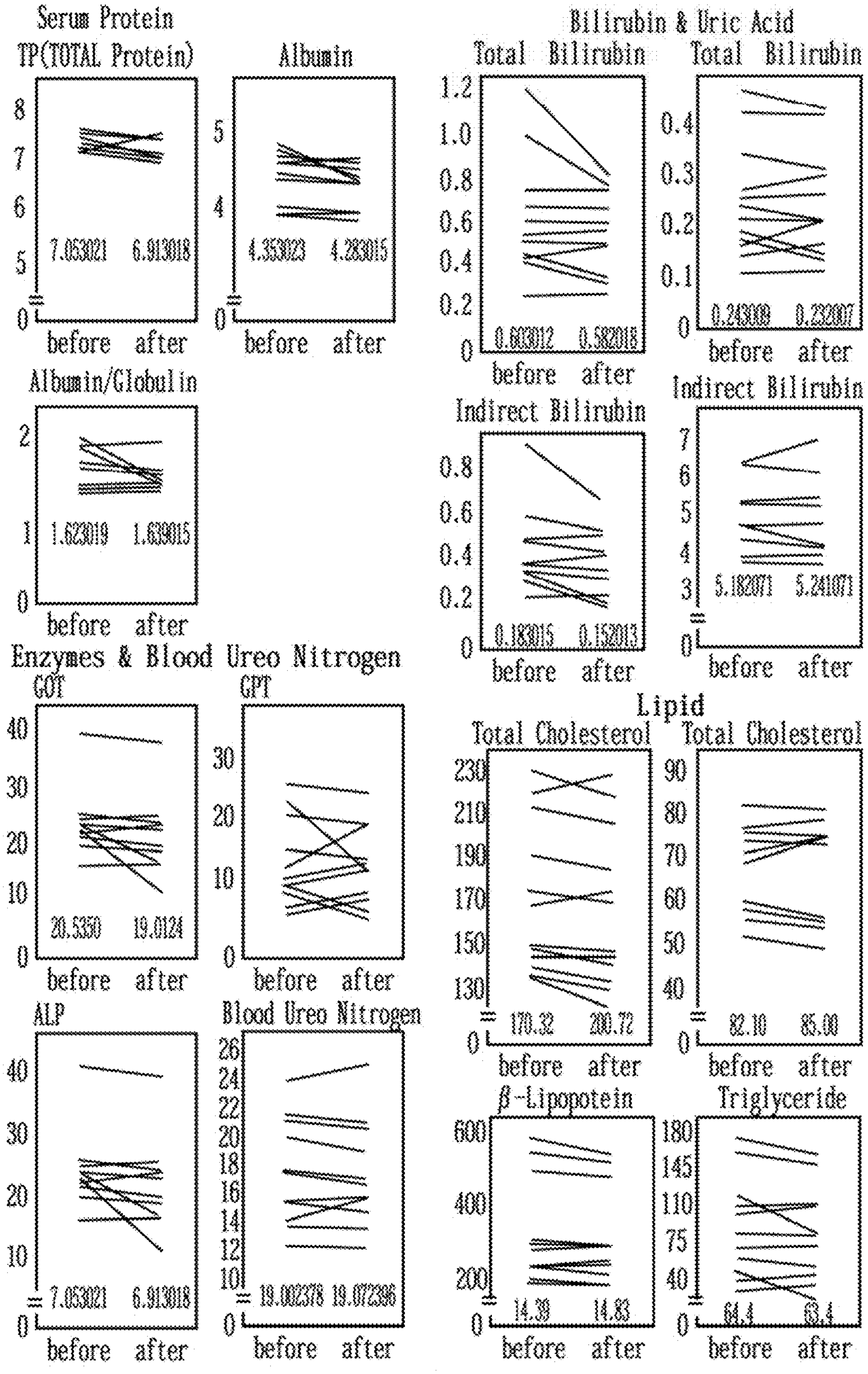
Figure 29:
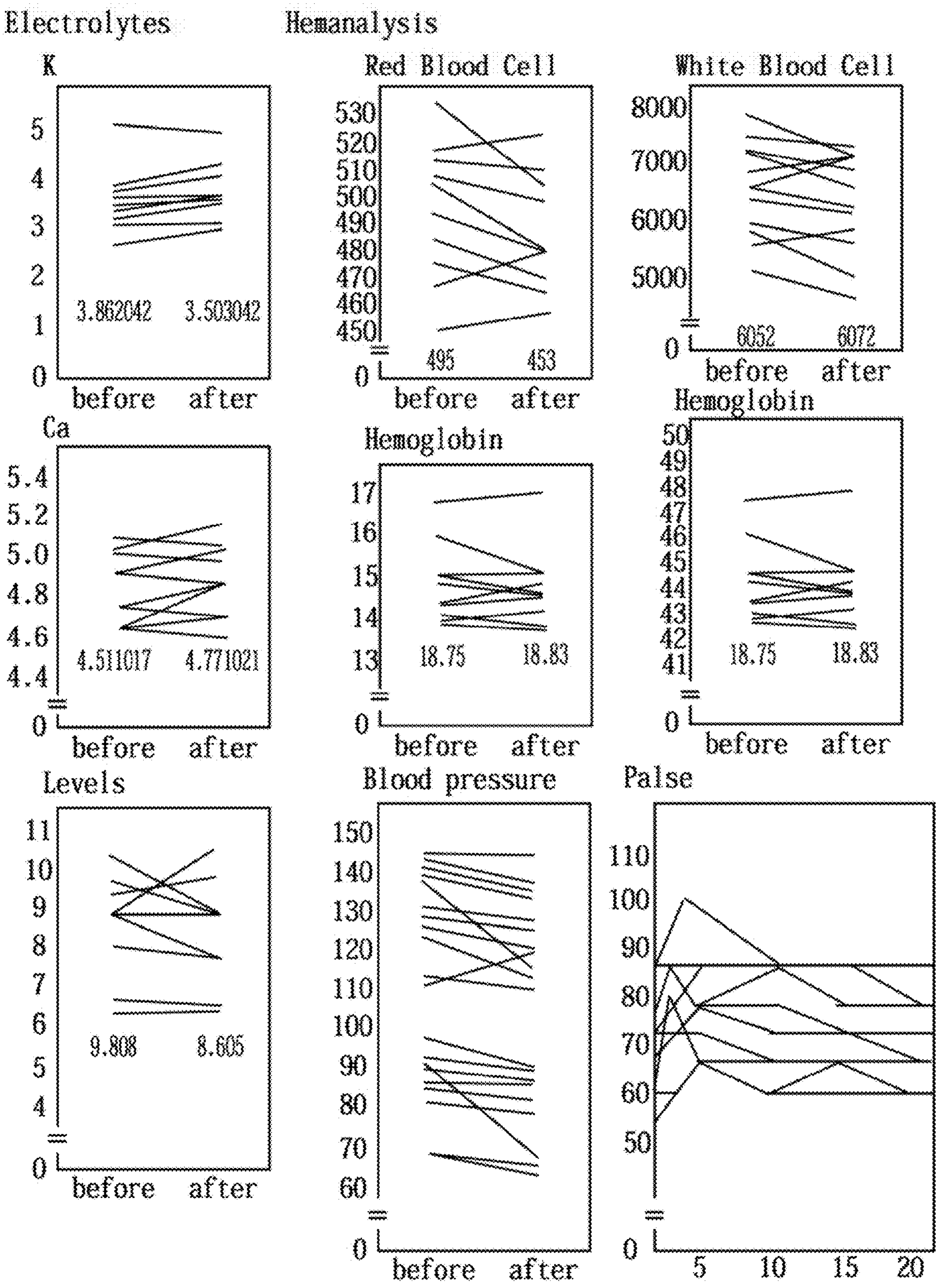

Furthermore, University of Tsukuba conducted various kinds of blood tests as shown in FIG. 27, FIG. 28 and FIG. 29. As a result, the University of Tsukuba obtained results that the apparatus of the present invention has the effect to improve blood and lowering bad cholesterol.

Figure 30:
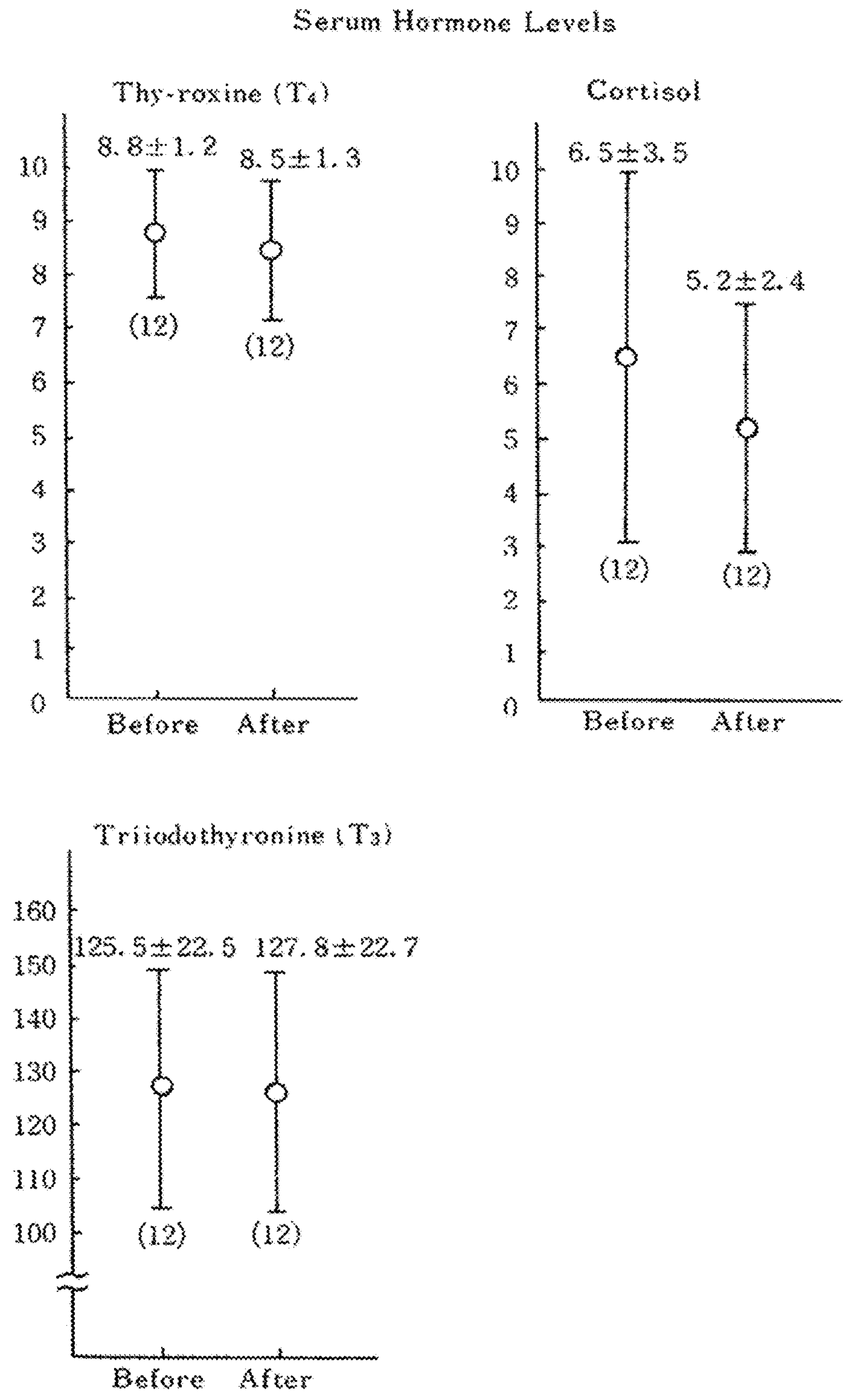

The most important result of this blood test is shown in FIG. 30. FIG. 30 shows measured values of hormone changes when the apparatus of the present invention is used. The results of the research at the University of Tsukuba are also reported as follows; "Thyroid hormone thyroxin (T4), decreased after use the apparatus of the present invention than before use of this apparatus of the present invention in 8 patients out of 12 patients. Cortisol, adrenocortical hormone, was lower by using the apparatus of this invention in 10 out of 12 patients than before using the present invented apparatus. It seems that the stress condition has subsided." In other words, it is an epoch making scientific proof that a stressed brain of a cancer patient subside by the apparatus of the present invention. This is the twelfth difference and effect of the present invention which is not found in public known other cancer treatment methods, including public known thermal methods.

Figure 31:
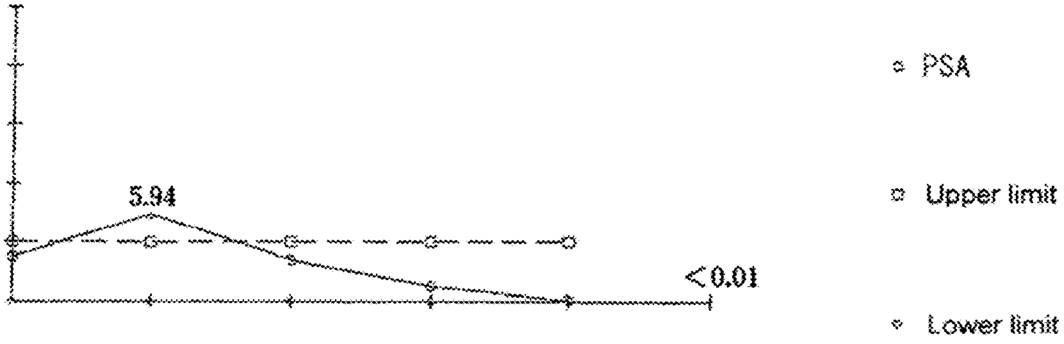

On the other hand, as a summary, the fact that the apparatus of the present invention is effective for eradicating ductal cancer is the fourteenth point different from public known thermal method. The experimental results on this are shown in FIG. 31.

Very bad face ductal cancer usually shows low PSA value, therefore, usually findings are delayed and cancer tends to spread to bones and other places. FIG. 31 shows PSA curve of the present inventor and ductal cancer patient himself who has applied the therapy method and the apparatus of the present invention. As you can see from the PSA curve, it was reduced to perfect level of PSA value. This data is the actually experimented data in a famous hospital of the body of present inventor that PSA drops down to 0.01 or less as shown by the curve in FIG. 31. This shows virtually killed ductal cancer whose face is very bad.

As described above, the therapy of the present invention is to inject the biocompatible material which is energy receptive and heat emissive to cancer cell in the body of a patient and give energy to the material from outside of cancer, and present invention include in the case that the equipment of FIGS. 8A-8D, FIG. 9 and FIGS. 10A-10F are not used.

The combination therapy of the present invention and a following public known therapy are also included in the present invention. For example, attaching $Fe_3O_4$ heating bag (Hokaron) to diapers, pants, briefs and G-string. Public known microwave heating device, heating by immersing in a bath of high temperature such as 41° C. for more than 15 minutes, drinking iodine milk by patients, surgical operation, DA VINCI ROBOT®, anticancer medicine, hormone therapy, for example, GONAX®, radiation therapy such as IMRT, VMAT, heavy particle beam, antibody medicine, molecular targeted drug, treatment to make cells from iPS that attack cancer cells and transplant them to patients, use of an Immune checkpoint inhibitors "Nivolumab" to make use of the body's immune mechanism, Immune checkpoint inhibitor "Pembrolizumab", T cell antibody drug "Mogamulizumab", T cell genetic engineering, TCR therapy, "Light ray immunotherapy" which is injecting the material which generates heat by LED or infrared ray from outside and a protein (antibody) that binds to the cancer cell, injection of alpha radiation, traditional Chinese medicine, various combination with the above many therapies and other modifications are conceivable, these are also included in the present invention.

INDUSTRIAL APPLICABILITY

The present invention is the result of research by the inventor who gets Ductal Cancer with his own body. As noted here, it was proved the therapy of the present invention has killed ductal cancer using the present inventor's own body, and CR (complete response) without side effects was proved. In addition, the present inventor, as honorable chairman of Walt Disney Children's Cancer Hospital, and US Beat Cancer Association, Florida Hospital World Cabinet and professor of many leading universities, the therapy and the apparatus of the present invention will save many worldwide cancer patients.

Since the present invention is possible to overcome difficult cancer and many other diseases, Health care and other national medical budgets can be saved and contributes to the worldwide humankind. Therefore industrial applicability is extremely large.

EXPLANATION OF SIGN

1 Radio wave transmitter
2 Radio wave
3 Ordinary cell
4 Cancer cell
5 Cold blood flow
6 Prostate
7 Bladder
8 Urethra
9 Rectum
10 Prostate cancer
11 Ductal cancer
12 Energy receptive and heat emissive material of the present invention
13 Vessels around the cancer comes from heat
14 Cancer patient
15 The direction of pull and push of the waist part 18
16 Energy dispatcher, for example, far infrared ray heater on buttocks
17 Energy dispatcher, for example, far infrared ray heater on back waist
18 Energy dispatcher, for example, far infrared ray heater on abdomen
18' Position of lifted 18
19 An applicator injection to insert a needle for a material of the present invention which receive energy from outside and emit heat to cancer cell.
20 Gun trick for a material of the present invention which receive energy from outside and emit heat to cancer cell in patient body.
21 Energy, for example, far infrared rays from the abdomen
22 Person who inserts a material which is energy receptive and that emissive into patient body.
23 Anal insertion ultrasonic transmitter probe
24 Compressor
25 Condenser pipe as heater
26 Motor driving a compressor
27 Top Actuator (cooling head by evaporator)
28 Mind Stabilizer
29 Mind Stabilizer pillow surface made by flexible rubber sheet mixed with aluminum powder
30 Low heat indicator lamp
31 Medium heat indicator lamp
32 High heat indicator lamp
33 Light to illuminates a back of a knee
34 Energy, for example, such as far infrared rays emitted to a back of waist
35 Energy, for example, far infrared rays emitted from the seat (16) to the perineum portion
36 Concentrator
37 Rear casters
38 Front foot
39 Foot Heat Actuator (foot heating stand)
40 Belt (belly band) connecting to and supports energy, for example, far infrared rays dispatcher on the waist (18), (18')
41 Front shield
42 Main power switch
43 Energy, for example, far infrared ray intensity step change and power on switch
43' Power off switch of the above

44 Refrigerant pipe
45 Shudder
46 Storage recess of waist pad
47 Hinge of angle change of waist pad
48 Robot main body (main apparatus of the present invention)
49 Back rest
50 Sheet for Condensation absorber pillow surface
51 Seat surface
52 Protector of pillow surface (29)
53 Fastener of an absorber seat (50) of Mind Stabilizer pillow surface
54 Concentrator's plug-in leg
55 Concentrator insertion hole
56 Rear receptacle
57 Insert plug
58 Front receptacle
59 Female plug
60 Power cord
61 Ground wire
62 Male plug
63 Switch of energy, for example, far infrared ray irradiating for waist
64 Switch of energy, for example, far infrared ray irradiating for belly
65 Rear waist pillow
66 Cooled blood
67 Knee of a patient (14)
68 Semiconductor light emitting diode LED of knee back irradiation
69 Energy reflecting surface of an energy dispatcher, for example, infrared ray located at butt (seat)
70 Same as above, an energy reflecting surface of waist
71 Same as above, an energy reflecting surface of abdominal
72 Net of holding and through pass energy, for example, far infrared ray dispatcher provided of buttocks (seat)
73 Same as above, net of lumbar part
74 Same as above, net of abdominal part
75 Support portion of an energy dispatcher (18), for example, a far infrared ray provided on an extension of a waist-wound belt (40)
76 Aluminum U type case for holding semiconductor light emitting diode LED tape which irradiate to back of knee
77 Same as above, reverse U type plastic cover
78 Same as above, mode (M) strong or weak (I) switch (S)
79 Same as above, converter
80 Foot soles bone
81 Tibia bone
82 Femur bone
83 Ischium, pelvis bone
84 Movable energy dispatcher, for example, far-infrared ray, Tera Herz Frequency for diseases, for example, breast cancer and lung cancer
85 Power supply and holding cable for above
86 Dispatcher of energy, for example, far infrared ray, Tera Herz Frequency provided on the back
87 Direction of air conditioning wind (front)
88 Same as above (sideways)

What is claimed is:

1. A method for providing therapy treatment of cancer and other diseases comprising the steps of:

heating the feet of a patient to raise a blood temperature flowing in a blood vessel around a cancer cell or other diseased area to 41° C. or more; and dispatching energy from an outside energy source to a material injected inside the patient at or near the cancer cell or other diseased area, wherein energy is emitted from the material to treat the cancer cell or other diseased area.

2. The method of claim 1, wherein the heating the feet of the patient includes heating a sole of the feet of the patient with a heating element, and the method further comprises a step of cooling a head of the patient with a cooling device.

3. The method of claim 1, further comprising a step of providing light from a light source to a back of a knee area of the patient.

* * * * *